(12) United States Patent
Montenegro et al.

(10) Patent No.: US 12,359,150 B2
(45) Date of Patent: Jul. 15, 2025

(54) ENZYMATIC SMOOTHING OF BEVERAGES

(71) Applicant: Voodoo Scientific USA, Inc., San Pedro, CA (US)

(72) Inventors: Joana Montenegro, San Pedro, CA (US); Martin Duncan Enriquez, San Pedro, CA (US)

(73) Assignee: Voodoo Scientific USA, Inc., San Pedro (CA)

( * ) Notice: Subject to any disclaimer, the term of this patent is extended or adjusted under 35 U.S.C. 154(b) by 0 days.

(21) Appl. No.: 18/532,529

(22) Filed: Dec. 7, 2023

(65) Prior Publication Data
US 2024/0191164 A1   Jun. 13, 2024

Related U.S. Application Data

(60) Provisional application No. 63/386,431, filed on Dec. 7, 2022.

(51) Int. Cl.
| | |
|---|---|
| *C12G 3/08* | (2006.01) |
| *C12G 3/021* | (2019.01) |
| *C12G 3/07* | (2006.01) |
| *C12N 9/02* | (2006.01) |

(52) U.S. Cl.
CPC .............. *C12G 3/08* (2013.01); *C12G 3/021* (2019.02); *C12G 3/07* (2019.02); *C12N 9/0008* (2013.01); *C12Y 102/01003* (2013.01); *C12Y 102/01004* (2013.01)

(58) Field of Classification Search
CPC . C12G 3/08; C12G 3/07; C12G 3/021; C12N 9/0008
See application file for complete search history.

(56) References Cited

U.S. PATENT DOCUMENTS

| | | | |
|---|---|---|---|
| 2,088,585 A | * | 8/1937 | Chambers ................ C12H 1/16 426/238 |
| 4,092,434 A | | 5/1978 | Yoshizumi et al. |
| 5,869,114 A | | 2/1999 | Murray et al. |
| 6,468,567 B1 | | 10/2002 | Rangel-Aldao et al. |
| 11,248,198 B2 | | 2/2022 | Bassoli |
| 2021/0292688 A1 | | 9/2021 | Rice et al. |
| 2022/0154113 A1 | | 5/2022 | Rice et al. |
| 2022/0259531 A1 | | 8/2022 | Williams |

FOREIGN PATENT DOCUMENTS

| | | |
|---|---|---|
| EP | 0832974 A2 | 4/1998 |
| EP | 0773285 B1 | 12/2002 |
| JP | 7209679 B2 | 1/2023 |
| JP | 2023128906 A | 9/2023 |
| WO | 2009094614 A1 | 7/2009 |
| WO | 2019242631 A1 | 12/2019 |

OTHER PUBLICATIONS

International Search Report and Written Opinion issued in International Application No. PCT/US2023/082901, mailed on Apr. 5, 2024, 9 pages.

\* cited by examiner

*Primary Examiner* — Vera Stulii
(74) *Attorney, Agent, or Firm* — Dorsey & Whitney LLP

(57) ABSTRACT

Methods of producing a consumable alcoholic product involve utilizing one or more enzymes to reduce or remove an oral pain response otherwise experienced upon consumption of the product. Methods involve admixing at least one oxidase with a fermentate and optionally distilling the fermentate to produce a consumable alcoholic product, such as a distilled alcohol. Methods involve admixing at least one oxidase comprising an aldehyde dehydrogenase.

20 Claims, 16 Drawing Sheets

Specification includes a Sequence Listing.

ENZYMATIC SMOOTHING OF BEVERAGES

CROSS-REFERENCE TO RELATED APPLICATIONS

This application claims priority to U.S. Provisional Patent Application No. 63/386,431, titled "Enzymatic Smoothing of Beverages" and filed on Dec. 7, 2022, the entire contents of which are incorporated herein.

TECHNICAL FIELD

The present disclosure is directed to the field of consumable beverages and systems and methods of their production. Implementations include methods of producing improved consumable beverages by adding at least one dehydrogenase enzyme to the beverage during or after production

SEQUENCE LISTING

The present disclosure further incorporates by reference the Sequence Listing submitted herewith. The Sequence Listing .xml file, identified as file name P305897US02.xml, is 24,440 bytes in size and was created on Nov. 23, 2023. The Sequence Listing, electronically filed herewith, does not extend beyond the scope of the specification, and does not contain new matter.

BACKGROUND

Many consumable beverages have an unpleasant harshness quality that, although typically accompanied by appealing flavors, may be readily detectable and overwhelming to consumers who may, as a result, create cocktails or consume the beverages together with salt, limes, etc. to mask the harshness. Distilled alcoholic beverages, for example, often have a noticeable harshness or "bite" that elicits a mild pain response in the mouth/throat/oral cavity of a consumer during consumption. Acutely aware of this problem, alcohol producers have endeavored to remove harsh notes from distilled alcoholic beverages by implementing one or more mellowing or smoothing techniques during or after the distillation process, just a few examples of the latter involving aging the distilled product, dripping the distilled product through a carbon filter, and/or adding flavors to the distilled product to mask its harshness. While these techniques may soften harshness levels to some extent, they do not eliminate or reduce them to undetectable levels. These methods are also energy intensive and time consuming.

Harshness qualities are not limited to alcohols, either, as they are commonly detected during the consumption of a range of beverages, examples of which include a variety of non-distilled alcohols, coffee, and tea.

Accordingly, new techniques for minimizing and even eliminating the unpleasant harshness of a range of consumable beverages and beverage components are needed.

SUMMARY

The present disclosure describes devices, systems and associated methods for producing improved consumable beverages by adding at least one dehydrogenase enzyme to the beverage or beverage component during production. In accordance with embodiments described herein, a method of producing a distilled alcoholic beverage may involve forming a mash mix—the substrate providing fermentable sugars for the yeast, fermenting the mash mix to form a fermentate, admixing at least one dehydrogenase with the fermentate, and distilling the fermentate to form a distilled ethanol comprising or formulated for inclusion in the distilled alcoholic beverage.

In some examples, the method further involves admixing at least one cofactor with the fermentate. In some examples, the at least one cofactor includes a dinucleotide cofactor, which may comprise NAD+ and/or NADP. In some examples, the cofactor is added at a loading level of about 1 mg/L of a fermentation volume to about 2 g/L of a fermentation volume. In some examples, the dehydrogenase includes an aldehyde dehydrogenase, which may be a native aldehyde dehydrogenase or an engineered dehydrogenase. The aldehyde dehydrogenase may selectively oxidize aliphatic aldehydes, which may include C2-C10 aliphatic aldehydes. In some examples, the distilled alcoholic beverage may have a lower level of aliphatic aldehydes relative to the level of aliphatic aldehydes present in a distilled alcoholic beverage formed without admixing a dehydrogenase with the fermentate. In some examples, the level of aliphatic aldehydes present in a distilled alcoholic beverage formed without admixing at least one dehydrogenase with the fermentate ranges from a concentration in a range spanning ppm to ppb. In some examples, the aldehyde dehydrogenase may selectively oxidize saturated and unsaturated aldehydes with an electrophilic index matching the nucleophilic index of the cysteine in the TRPA1 receptor.

In some examples, the method further involves adjusting the pH of the fermentate to about 5.0 to about 7.0. In some examples, the pH of the fermentate may not be adjusted. In some examples, the dehydrogenase is added at a loading level of about 1 mg/L to about 2 g/L of a fermentation volume. In some examples, the method also involves aging the distilled ethanol in a barrel. In some examples, the mash mix is fermented for about up to about 5 days. In some examples, the mash mix includes one or more of corn, rye, rice, barley, wheat, agave, dextrin, potato, fruit, molasses, water, an enzyme, or one or more additional organic feedstocks for yeast. In some examples, the ethanol concentration of the distilled ethanol is about 20% to about 95%. In some examples, the ethanol concentration of the fermentate is about 1% to about 20%.

In accordance with embodiments described herein, a system of producing a distilled alcoholic beverage includes a mash tun configured to agitate and heat a mash mix, a fermentation tank configured to ferment the mash mix and form a fermentate, at least one dehydrogenase configured for admixing with the fermentate, a still apparatus configured to heat the fermentate and form a fermentate vapor, a condenser apparatus configured to cool the fermentate vapor and form a distilled ethanol, and a collection apparatus to collect the distilled ethanol.

In some examples, the system further includes a barrel configured to receive and store the distilled ethanol pursuant to an aging process and in some examples the distillate is not aged and hence bottled right away. In some examples, the system also includes at least one cofactor configured for admixing with the fermentate. In some examples, the at least one cofactor comprises a dinucleotide cofactor, such as NAD+ or NADP. The dehydrogenase may include an aldehyde dehydrogenase, which may be native or engineered, and which may selectively oxidize aliphatic aldehydes, including C2-C10 aliphatic aldehydes. The system may also include at least one base configured to increase a pH of the fermentate. In some examples, components of the mash mix include one or more of corn, rye, rice, barley, wheat, agave, dextrin, potato, fruit, molasses, water, an enzyme, or one or more additional organic feedstocks for yeast. In some examples, the system further includes one or both of a grinder apparatus or a press apparatus configured to grind or press one or more of the components of the mash mix.

In accordance with embodiments of the present disclosure, a fermentate formed pursuant to a method of producing a distilled alcoholic beverage may include a mash mix that includes one or more of corn, rye, rice, barley, wheat, agave, dextrin, potato, fruit, molasses, water, an enzyme, a sugar source, or sucrose. The fermentate may also include at least one aldehyde dehydrogenase, as well as ethanol at a concentration of about 1% to about 20%.

In some examples, the fermentate further includes a dinucleotide cofactor. The aldehyde dehydrogenase may be a native or engineered aldehyde dehydrogenase. In some examples, the aldehyde dehydrogenase is present at a concentration of about 1 mg/L to about 2 g/L of the fermentate. In some examples, the dinucleotide cofactor may be present at a concentration of about 1 mg/L of a fermentation volume to about 2 g/L of the fermentate.

In accordance with embodiments of the present disclosure, a method of producing a distilled alcoholic beverage may involve forming a mash mix, fermenting the mash mix to form a fermentate, distilling the fermentate to form a distilled ethanol, and admixing at least one dehydrogenase with the distilled ethanol to form the distilled alcoholic beverage.

In some examples, the method further involves admixing at least one cofactor with the distilled ethanol. The cofactor may include a dinucleotide cofactor, such as NAD+. In some examples, the dehydrogenase includes an aldehyde dehydrogenase, which may be native or engineered. The aldehyde dehydrogenase may selectively oxidize aliphatic aldehydes, such as C2-C10 aliphatic aldehydes. In some examples, the distilled alcoholic beverage has a lower level of aliphatic aldehydes relative to a level of aliphatic aldehydes present in a distilled alcoholic beverage formed without admixing at least one dehydrogenase with the distilled ethanol. In some examples, the level of aliphatic aldehydes present in a distilled alcoholic beverage formed without admixing at least one dehydrogenase with the distilled ethanol ranges from a concentration in a range spanning ppm to ppb. In some examples, admixing the dehydrogenase with the distilled ethanol is performed in a barrel or in a bottle, after distilling. In some examples, the mash mix includes one or more of corn, rye, rice, barley, wheat, agave, dextrin, potato, fruit, molasses, water, an enzyme, or an organic feedstock for yeast. In some examples, the ethanol concentration of the distilled ethanol is about 20% to about 95%.

In accordance with embodiments described herein, a method of producing a consumable alcoholic product may involve forming a mash mix, fermenting the mash mix to form a fermentate, admixing at least one oxidase with the fermentate, and collecting the fermentate for inclusion in the consumable alcoholic product.

In some examples, the at least one oxidase may include or consist of an aldehyde dehydrogenase. In some examples, the aldehyde dehydrogenase may be or include a native aldehyde dehydrogenase. In some examples, the aldehyde dehydrogenase may be or include an engineered or modified aldehyde dehydrogenase. In some examples, the aldehyde dehydrogenase selectively oxidizes aliphatic aldehydes. In some examples, the aliphatic aldehydes may include C2-C10 aliphatic aldehydes. In some examples, the consumable alcoholic product may have a lower level of aliphatic aldehydes relative to a level of aliphatic aldehydes present in a consumable alcoholic product formed without admixing at least one dehydrogenase with the fermentate. In some examples, the level of aliphatic aldehydes present in a consumable alcoholic product formed without admixing at least one oxidase with the fermentate ranges from a concentration spanning ppm to ppb.

In some examples, methods may further involve admixing at least one dinucleotide cofactor with the fermentate. In some examples, the dinucleotide cofactor may be or include NAD+, NADP+, or both. In some examples, methods may further involve distilling the fermentate to form a distilled ethanol comprising or formulated for inclusion in the consumable alcoholic product. In some examples, methods may further involve aging the distilled ethanol in a barrel. In some examples, an ethanol concentration of the distilled ethanol may be about 20% to about 95%. In some examples, the consumable alcoholic product may be or include a beer. In some examples, methods may further involve adjusting a pH of the fermentate to about 5.0 to about 7.0. In some examples, the pH of the fermentate may not be adjusted. In some examples, the at least one oxidase may be added at a loading level of about 5 mg/L to about 2 g/L of a fermentation volume. In some examples, fermenting the mash mix may involve fermenting the mash mix for about up to about 5 days. In some examples, the mash mix may include one or more of corn, rye, rice, barley, wheat, agave, dextrin, potato, fruit, molasses, water, an enzyme, a sugar source, or sucrose. In some examples, an ethanol concentration of the fermentate may be about 1% to about 20%.

DETAILED DESCRIPTION

Figure 1:
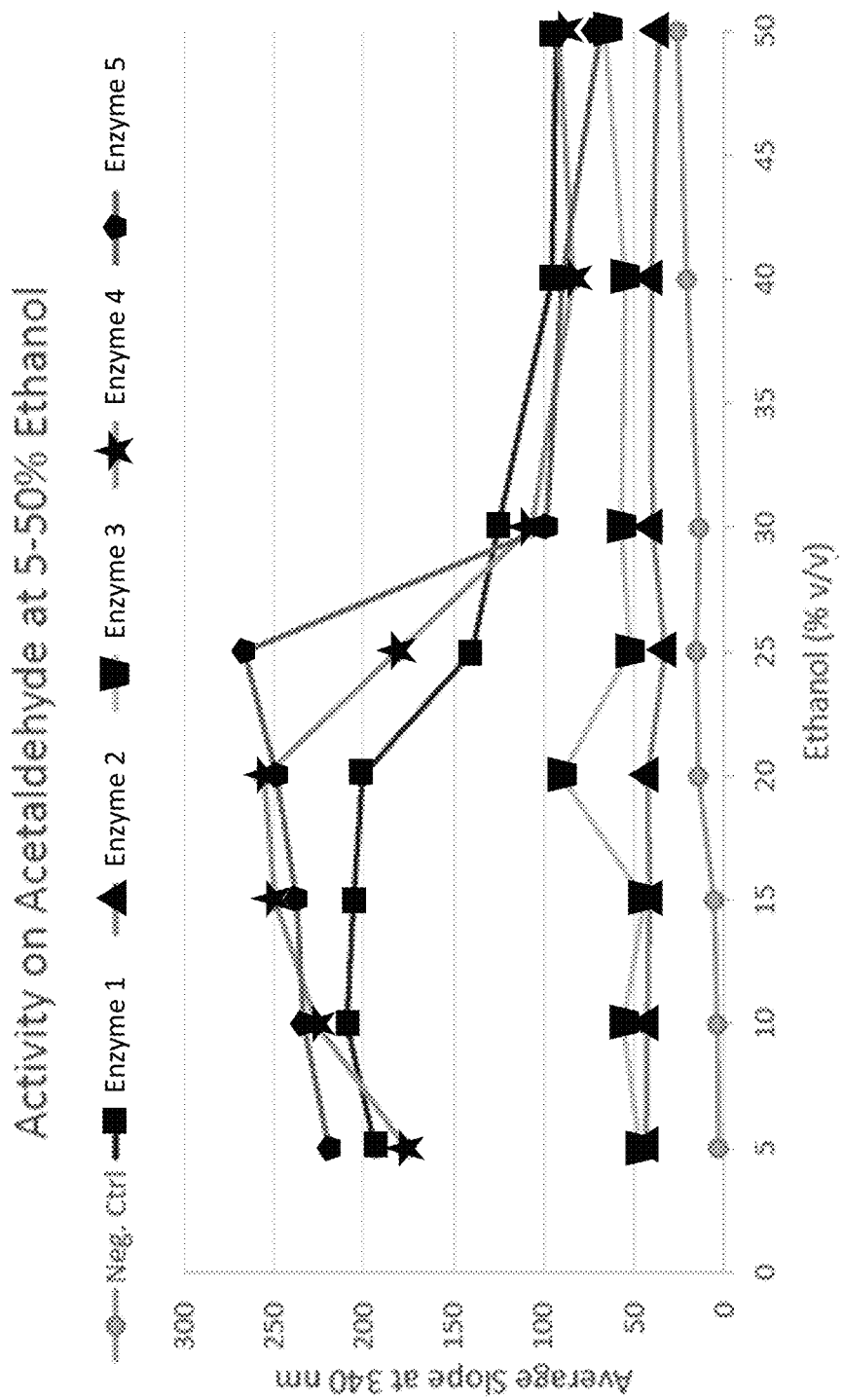
FIG. 1 is a graph showing the activity levels of five different aldehyde dehydrogenases in the presence of acetaldehyde in accordance with embodiments of the present disclosure.

Definitions:

As used herein, the term "beverage" encompasses a variety of consumable products, non-limiting examples of which may include distilled alcoholic beverages (e.g., vodka, whiskey, rum, brandy, gin, tequila, baijiu, spirits, cocktails, etc.), non-distilled alcoholic beverages (e.g., beer, wine, cider, sake, hard seltzer etc.), coffee, and tea. While not consumed alone, ethanol used as a solvent for flavors may also be treated in accordance with the disclosed principles. Reference is made herein primarily to distilled alcoholic beverages and associated production methods only for ease of illustration.

Relatedly, the term "beverage" may be used in reference to a final beverage product ready for consumption (e.g., a distilled alcoholic beverage), a beverage component (e.g., ethanol), or an intermediate composition formed during beverage production (e.g., a fermentate, which may itself be defined as a product resulting from the fermentation of organic feedstock).

As used herein, the term "dehydrogenase" may refer to one or more dehydrogenases, which may be or include an aldehyde dehydrogenase. The term may also refer to a broader class of dehydrogenases, oxidases, and oxidoreductases, the latter of which may include a variety of enzymes that catalyze redox transformations involved in biosynthesis, intermediary metabolism, and detoxification. Substrates of these enzymes may include glucose, steroids, glycosylation end products, lipid peroxidation products, and/or environmental pollutants. In some examples, the term "enzyme" may be synonymous with dehydrogenase, e.g., aldehyde dehydrogenase, and may refer to an enzyme composition, which may comprise two or more enzymes and/or non-enzymatic components. In some examples, the term "enzyme" may include an oxidase that selectively acts on specific compounds generated by lipid peroxidation that occurs as a result of oxidative stress exerted on yeast during an alcohol production process.

As used herein, "harshness" may refer to the unpleasant, harsh bite of a beverage that elicits a mild pain response in the mouth and throat of a person upon consuming the beverage. Harshness may not, in some embodiments, refer to the burn/warmth of ethanol or to a negative flavor per se, such as a flavor, composition or substance sometimes referred to as a congener or fusel oil.

As used herein, a "user" may refer to a recipient, producer or handler of the enzyme compositions disclosed herein. A user may also refer to a person performing or managing a beverage production process in accordance with the disclosed methods.

Singular forms of various terms may encompass the plural forms of the same terms. For example, it should be understood that the term "enzyme" may also encompass the term "enzymes" and "enzyme systems."

In the alcoholic beverage industry, conventional wisdom has taught that improving distillation techniques provides the best approach to enhancing beverage smoothness. Distillation, barrel aging, filtration, carbon filtration and/or supplementation with additional masking flavors, for example, encompasses many of the preexisting approaches to combating harshness. The disclosed approaches defy conventional wisdom and embody substantial improvements relative to preexisting techniques, which lack the sensitivity and specificity necessary to eliminate the previously unrecognized harshness-causing compounds present within consumable beverages, often at very low levels.

The appeal of alcoholic beverages, especially of the distilled variety, has been dampened by the harshness and painful "bite" that commonly accompanies consumption. From the lowest quality product to the highest, most expensive bottles, this negative sensory experience is never fully overcome by even the most rigorous production techniques. This disclosure is based on the discovery, not made prior, of precisely which compounds cause the harsh bite sensation in consumers and the novel methods used to combat them and produce fully smooth spirits lacking the harsh bite typical of spirits or other consumable beverages not treated in accordance with the methods disclosed herein. To date the only methods used to even attempt reduction of harshness are distillation, filtration, or aging, and they are largely ineffective. Additionally, in the limited instances in which enzymes have been used during the production of particular alcoholic beverages, they have been confined to distinct compositions and methods capable only of increasing fermentable sugar content or reducing liquid viscosity. Such narrow applications do not result in the reduction of beverage harshness, as contemplated herein. Never has the connection been made between the harsh bite sensory experience associated with alcohol consumption, the pain receptors involved in that experience, and the noxious compounds generated in fermentation that are agonists to this specific pain receptor. As a result, the disclosed use of one or more the disclosed enzymes, such as a dehydrogenase enzyme, to selectively target these noxious compounds without affecting other flavors or aromas in consumable beverages, has not been performed.

As humans, there are three categories of sensory experience: the experience of flavors (taste), the olfactory experience of aroma perception, and somatosensory, which is responsible primarily for sensations such as pain. The Food and Beverage Industry focuses heavily on the first two but not on the latter, which embodiments of the disclosed compositions, methods, and systems address. In the production of alcoholic or distilled alcoholic beverages, a mash (a recipe consisting of organic matter that yeast will use as a source of sugars for fermentation) is created to be fermented by a yeast. The yeast tends to undergo oxidative stresses as the level of ethanol rises as fermentation progresses. This stress leads to lipid peroxidation reactions, ending in noxious compounds discovered and combatted according to the embodiments disclosed herein. Given that the source of these irritant compounds is lipid peroxidation of yeast cell membranes, they are present independently of the type of alcoholic beverage being produced. Humans will experience a mild pain response in the form of the harsh bite discussed herein, in reaction to these compounds, which are noxious electrophilic, often aldehydes. This disclosure provides compositions, methods, and systems that effectively target and eliminate these irritants responsible for the unpleasant harshness associated with consumable alcohols, thereby creating truly smooth alcoholic beverages, including beverages typically categorized as premium beverages, among others, as demonstrated via the analytical and sensory tests disclosed herein.

Embodiments involve use of an aldehyde dehydrogenase to target very specifically the products of lipid peroxidation of the yeast cell membrane that occurs once the yeast undergoes oxidative stresses towards the end of its alcoholic fermentation. This lipid peroxidation leads to a series of compounds, many of which are aliphatic aldehydes such as malondialdehyde or nonenal, as examples, that are well known as triggers of the TRPA1 receptor (transient receptor potential cation channel, subfamily A, member 1 or ankyrin 1). TRPA1 is not a flavor receptor, but a pain receptor responsible for the harsh "bite" sensation, as further set forth below. The harshness is not a flavor that is tasted, but rather a mild pain sensation in response to the presence of noxious compounds such as aliphatic saturated or unsaturated aldehydes. These compounds are eliminated by the disclosed enzymatic oxidation of the carbonyl groups into carboxylic acids which are weak organic acids, often precursors to the formation of esters which are desirable in distilled alcoholic beverages. The disclosed approaches do not alter the flavor profile of alcoholic beverages, but rather eliminate the harshness of such beverages, thereby creating a truly smooth beverages.

Not all aldehydes are responsible for the pain sensation experienced, as there are myriad of aldehydes in existence. Many are responsible for desirable flavors (e.g., cinnamaldehyde), some are responsible for off-flavors (e.g., certain aldoses), and some are toxic. The toxicity is dependent on the electrophilicity and stearic hindrance of the aldehyde. The TRPA1 receptor is designed to detect and react only to aldehydes that have a specific toxic electrophilicity to affect living cells negatively. Embodiments disclosed herein may act on these toxic noxious aldehydes, specifically, while leaving the desirable varieties intact.

Disclosed Embodiments

Disclosed herein are methods, systems and associated reagents, ingredients and apparatuses for eliminating, minimizing or reducing the harshness levels detected by consumers during consumption of a range of consumable beverages, non-limiting examples of which may include distilled alcoholic beverages. Embodiments may involve adding at least one natural or engineered enzyme to a beverage or component thereof during or after its production. The enzyme may comprise one or more dehydrogenases, such as at least one aldehyde dehydrogenase. In embodiments featuring an aldehyde dehydrogenase, the dehydrogenase may be added before, during, and/or after the commencement of a fermentation process, and/or after the distillation process in embodiments related to the production of distilled alcoholic beverages. The dehydrogenase may decrease, through oxidation, the total content of one or more aldehydes present in the beverage, including aldehydes present at very low levels. Specifically targeted aldehydes may include aliphatic, electrophilic aldehydes, such as C2-C10 aliphatic aldehydes. The dehydrogenase enzyme may not act on aldehydes are responsible for flavor perception by humans; it may selectively act only on the aldehydes identified herein as irritants responsible for the harsh bite and pain response in consumers. Accordingly, by reducing the amount of one or more of these specific aldehydes, the harshness of the final beverage product may be eliminated or reduced to levels undetectable or substantially undetectable to most consumers, while the intended flavor of the product may be preserved.

Enzyme Compositions

The enzyme(s) utilized to reduce or eliminate the harshness typical of many consumable beverages may include at least one dehydrogenase, such as at least one aldehyde dehydrogenase. The enzyme(s) may selectively catalyze the oxidation of one or more electrophilic compounds identified by the inventors as causal agents or contributors to beverage harshness without also targeting compounds that contribute to desirable flavors or qualities of a final beverage product, even though both types of compounds may reside in the same chemical class. For example, the methods disclosed herein may not affect aldehydes that are positive flavors due to stearic hindrance. Embodiments may selectively target one or more carbonyl groups, e.g., aldehydes, for oxidation, thereby converting the targeted compounds into carboxylic acids. The compounds targeted by the enzyme(s) may be present at very low levels in a beverage or beverage component. Accordingly, the disclosed enzyme(s) may exhibit high levels of specificity and sensitivity. For ease of illustration, the singular term "enzyme" will be primarily used hereafter, but it should be understood that "enzyme" may refer to one or more enzymes or enzymatic systems.

In some embodiments, the enzyme may be substantially native (or wild-type) in amino acid composition, protein conformation, and activity. Native enzymes exhibiting the substrate specificity and sensitivity necessary to remove the harshness from distilled alcoholic beverages were discovered after extensively testing 15 different aldehyde dehydrogenases for their activity under conditions typical of commercial alcoholic fermentation and distillation. While one native enzyme exhibited the most significant harshness reduction overall, additional dehydrogenases from the original 15 test enzymes were also effective, including all 15 enzymes used individually or in combinations during an alcohol production process, indicating that aldehyde dehydrogenases, as an enzymatic class, may effectively reduce the harshness associated with alcoholic beverage consumption when utilized in accordance with the methods described herein. The amino acid sequences of the 15 enzymes evaluated to show this effect correspond to SEQ ID NOS: 1-15. In embodiments, enzymes implemented pursuant to the disclosed methods for effectively reducing beverage harshness may be about 80%, 85%, 90%, 95%, 99% or 100% identical to any one of SEQ ID NOS: 1-17.

Embodiments may additionally or alternatively feature an artificially modified or engineered enzyme, which may differ in amino acid composition, protein conformation, and/or activity from a native enzyme. Embodiments may include enzyme compositions and systems containing a mixture of one or more native and/or engineered enzymes. Native and engineered varieties may also be included in separate compositions utilized concurrently during a beverage production process, depending on specific fermentation conditions and the relative concentration of the specific compounds being targeted. In embodiments, engineered enzymes implemented pursuant to the disclosed methods of reducing beverage harshness may be about 80%, 85%, 90%, 95%, 99% or 100% identical to any one of SEQ ID NOS: 1-17, or about 80%, 85%, 90%, 95%, 99% or 100% to other native dehydrogenases.

The form of the native enzyme that exhibited the most significant harshness reduction during the experiments described below (identified as Enzyme 2, 54.1 kDa) has an amino acid sequence corresponding to SEQ ID NO: 6. One or more additional enzymes effective to significantly reduce beverage harshness according to the disclosed approaches may be at least about 80%, 85%, 90%, 95%, 99% or 100% identical to SEQ ID NO: 6. An additional native enzyme that exhibited significant harshness reduction in the experiments described below (identified as Enzyme 3, 54.0 kDa) has an amino acid sequence corresponding to SEQ ID NO: 8. One or more additional native enzymes exhibiting effective harshness reduction when utilized according to the disclosed methods may be at least about 80%, 85%, 90%, 95%, 99% or 100% identical to SEQ ID NO: 8. The native enzyme identified as Enzyme 2 in the experiments described below may exhibit greater pH tolerance than the native enzyme identified as Enzyme 3, but both enzymes are effective harshness reducers responsible for the significant reduction in the harsh bite of consumable alcohols and alcohol components. The remaining enzymes subjected to the test conditions set forth below, corresponding to SEQ ID NOS: 1-5, 7, and 9-15 (which include the enzymes identified as Enzymes 1 and 4-15), may also be substantially or equally as effective, due at least in part to their substantial homology to each other and to Enzymes 2 and 3, along with other aldehyde dehydrogenases, as would be understood by one skilled in the art due at least in part to the enzymatic activity common to all aldehyde dehydrogenases characterized by the oxidation of aldehydes to carboxylic acids. Accordingly, while the experiments detailed herein evaluated a subset of the enzymes, the enzymes effective for driving harshness reduction according to the disclosed embodiments may include more, e.g., all or substantially all, dehydrogenases, including aldehyde dehydrogenases. The disclosed approaches are thus not limited to the specific enzymes tested in the experiments described below.

A native form of the enzyme used in accordance with embodiments disclosed herein may have a mass spanning from about 40 kDa to about 60 kDa, including up to about 41 kDa, to about 42 kDa, to about 43 kDa, to about 44 kDa, to about 45 kDa, to about 46 kDa, to about 47 kDa, to about 48 kDa, to about 49 kDa, to about 50 kDa, to about 51 kDa, to about 52 kDa, to about 53 kDa, to about 54 kDa, to about 55 kDa, to about 56 kDa, to about 57 kDa, to about 58 kDa, to about 59 kDa, or greater. Embodiments of the native enzyme may also have a mass spanning from about 53.5 kDa to about 57 kDa, including up to about 54.0 kDa, to about 54.5 kDa, to about 55.0 kDa, to about 55.5 kDa, to about 56.0 kDa, to about 56.5 kDa, or greater. Specific embodiments of the dehydrogenase may have a mass of about 54.1 kDa, about 57.5 kDa, or about 56.7 kDa.

The different properties exhibited by the native and engineered forms of the enzyme may vary. For example, an engineered enzyme may exhibit normal activity levels under conditions of reduced pH and/or elevated temperature and/or elevated ethanol concentration, for instance, while a native enzyme may exhibit a reduction in activity under the same conditions. In some embodiments, native forms of the enzymes, including those having an amino acid sequence substantially similar or identical to one or more of SEQ ID NOS: 1-17, may exhibit effective activity levels substantially equal to engineered forms of the enzyme. Different enzymes may also exhibit more or less enzymatic activity in a range of conditions. Accordingly, the beverage production parameters may be adjusted depending on which enzyme is used.

The engineered enzyme may maintain its activity under typical fermentation conditions, e.g., at pH levels ranging from about 3.0 to 6.0, temperatures ranging from about 15° C. to about 37° C., and ethanol concentrations ranging from 0 to 20%, e.g., about 12%, about 13%, about 14%, about 15%, about 16%, about 17%, about 18%, about 19%, or greater for post-distillation addition of the enzyme, for example up to about 25%, about 30%, about 35%, about 40%, about 45%, about 50%, about 55%, about 60%, about 65%, about 70%, about 75%, about 80%, about 85%, about 90%, or about 95% ethanol, or any level therebetween. In some examples, a native form of the enzyme may maintain approximately stable activity levels at elevated ethanol concentrations, including up to about 10% ethanol to about 11% ethanol, about 12% ethanol, about 13% ethanol, about 14% ethanol, about 15% ethanol, about 16% ethanol, about 17% ethanol, about 18% ethanol, about 19% ethanol, or greater.

The activity of native forms of the enzyme at lower pH levels may be less than that of engineered forms of the enzyme in some examples. For instance, a native form of the enzyme may exhibit detectable activity at pH levels between 3.5 and 7.0, but the optimal activity may be achieved at pH levels of about 6.0 to about 7.0. Accordingly, while native forms of the enzyme may exhibit sufficient activity levels at pH levels less than about 6.0, fermentation methods utilizing a native enzyme may involve increasing the pH levels of a fermentate up to or above 6.0, e.g., 6.7. In some embodiments, the enzymatic activity of one or more native forms of the enzyme, non-limiting examples of which include enzymes having any one of SEQ ID NOS: 1-17, may be substantially the same as one or more engineered forms of the enzyme at lower pH levels ranging from about 3.5 to about 7.0.

The enzyme composition may be dry or liquid. Embodiments of the enzyme composition may comprise a spray-dried or lyophilized powder, for instance, or a liquid solution comprised of powdered enzyme suspended in water and/or one or more buffers. In some examples, the enzyme composition, which may or may not include an added cofactor, may be immobilized on a solid substrate or structure. The pure enzyme content of the enzyme composition may vary, depending largely on the final form of the composition. For enzyme compositions in powder form, the enzyme activity may range from about 2 units/mg protein to about 5 units/mg protein, to about 10 units/mg protein, to about 15 units/mg protein, to about 20 units/mg protein, to about 25 units/mg protein, to about 30 units/mg protein, to about 35 units/mg protein, to about 40 units/mg protein, to about 45 units/mg protein, to about 50 units/mg protein, or greater, or any level therebetween.

The enzyme may be provided to a user in a variety of forms. In some examples, the enzyme may be provided in one or more vials, containers, or tubs. Embodiments may also feature a single-use add-pack containing the amount of enzyme needed for one round of a batch-wise beverage production process. Similar add-packs may also be provided for one-time addition to a continuous beverage production process. Numerous packs may thus be used for continuous production processes, with individual packs added at regular intervals throughout production, e.g., during or after fermentation, including after distillation.

As noted above, the enzyme(s) may exhibit high levels of substrate-specificity and sensitivity. In addition to ethanol, distilled alcoholic beverages generally contain trace amounts of hundreds of organic molecules, such as organic acids, other alcohols, ketones, esters, aldehydes, organic fats, and proteins, the sheer number and diversity of which significantly complicates any efforts to identify and effectively target only those compounds responsible for causing beverage harshness. In some examples, the enzyme may effectively reduce or even eliminate one or more harshness-causing aldehyde substrates present in a beverage or beverage component (e.g., fermentate) at only 500 ppm or less, for instance about 5 ppm to about 10 ppm, or even less, such as on the order of ppb.

Without being bound to any particular theory, the pain response triggered in consumers upon consuming certain harsh beverages may be attributed to activation of the trigeminal nerve, which is caused by activation of certain molecular receptors, such as TRPA1. TRPA1 is reactive to more than one compound and cannot be blocked using a masker or flavor blocker due to the nature of its mechanism of action, making it difficult to neutralize. As provided herein, it has been discovered that electrophilic, aliphatic compounds present within harsh beverages may be chiefly responsible for TRPA1 activation. Aliphatic molecules having a reactive carbonyl group, e.g., aldehydes, may form reversible covalent bonds with one or more cysteine residues present within the active site of TRPA1, thereby inducing the pain response caused by TRPA1 activation. Aliphatic molecules having $\alpha,\beta$ unsaturated bonds, in particular, may drive the most significant pain response. These compounds may cause significant trigeminal nerve activation at very low levels, e.g., on the order of ppm to ppb, that even the most sophisticated distillation techniques are unable to eliminate. The present discovery that such low substrate levels may be effectively targeted and enzymatically eliminated was surprising, especially in the context of distilled alcohol production, which requires the implementation of various processing parameters not traditionally conducive to enzyme function.

In the context of alcohol production, increases in ethanol production (during fermentation, for example), cause environmental stress impacting the lipid bilayer of yeast. Oxidative stress leads to increases in reactive oxygen species, which drives lipid peroxidation reactions and the corresponding production of noxious aldehydes, including hydroxynonenal, malondialdehyde, and acrolein, each of which tripper the TRPA1 pain receptor when consumed by humans.

Use of the disclosed enzymes in the disclosed methods and systems may prevent the covalent bond between the cysteine residue of TRPA1 and reactive carbonyl groups by catalyzing the conversion of the aliphatic compound(s) into carboxylic acids. By this mechanism, the disclosed methods may effectively reduce or eliminate the level of pain-inducing compounds present at very small, but noticeable levels in a variety of beverage products. In some examples, the enzyme(s) may catalyze the oxidation of multiple different substrates, e.g., multiple types of carbonyl electrophiles, non-limiting examples of which may include crotonaldehyde, octanal (e.g., n-octanal), nonanal (e.g., n-nonanal), dodecanal (e.g., n-dodecanal), and/or acetaldehyde. In some examples, oxidation of acetaldehyde may be catalyzed by the disclosed enzymes, but its reduction may have little to no impact on perceived harshness levels, unlike the aforementioned aliphatic aldehydes, especially of the C2-C10 variety.

Notably, enzyme-driven conversion of the targeted aldehydes into carboxylic acids may also result in the formation of ester precursors that may improve the taste and/or smoothness of the final beverage product in a manner previously achieved only through aging.

Methods of Reducing Beverage Harshness

Disclosed methods of reducing beverage harshness involve adding at least one of the disclosed enzymes to a consumable beverage or component thereof during a beverage production process. As noted above, the disclosed enzymes may be configured to catalyze the redox reaction of aldehydes responsible for the harshness of various beverages within the temperature, pH, and concentration ranges unique to alcoholic beverages, e.g., distilled alcoholic beverages. To reduce the concentration of aliphatic aldehydes and thus the overall harshness of the final distilled product, one or more enzymes may be added to one or more intermediate compositions formed during the alcohol production process, such as a fermentate or distillate, or a composition formed after distillation. Embodiments directed to the production of alcoholic beverages may generally involve mash formation, fermentation, optional distillation, and optional aging. The particular sub-processes implemented may depend on the final alcoholic product. For instance, embodiments featuring beer production do not include distillation, unlike embodiments featuring whiskey or vodka production.

Making the mash—The mash used for fermentation may include a variety of components in a range of amounts and concentrations. Components of the mash may vary based on the type of beverage being produced, e.g., wine, beer, vodka, gin, whiskey, bourbon, baijiu, rum, or any other consumable alcoholic beverage. Non-limiting examples of mash components may include one or more of: grains (e.g., corn, rye, rice, barley, wheat), agave, dextrin, potato, fruits (e.g., grapes), molasses, water, one or more enzymes, one or more organic feedstocks for yeast, and/or additional sugars (e.g., sucrose), sugar equivalents, or sugar sources having sugar concentrations ranging from about 0 wt % to 100 wt %, including less than 1 wt % up to about 5 wt %, to about 10 wt %, to about 15 wt %, to about 20 wt %, to about 25 wt %, to about 30 wt %, to about 35 wt %, to about 40 wt %, to about 45 wt %, to about 50 wt %, to about 55 wt %, to about 60 wt %, to about 65 wt %, to about 70 wt %, to about 75 wt %, to about 80 wt %, to about 85 wt %, to about 90 wt %, to about 95 wt %, or more, or any concentration therebetween.

The amount of each mash component may vary. For instance, embodiments featuring corn may include about 60 wt % corn up to about 65 wt % corn, to about 70 wt % corn, to about 75 wt % corn, to about 80 wt % corn, to about 85 wt % corn, to about 90 wt %, or any amount therebetween. Embodiments featuring rye or rye malt may include about 10 wt % rye malt up to about 12 wt % rye malt, to about 14 wt % rye malt, to about 16 wt % rye malt, to about 18 wt % rye malt, to about 20 wt % rye malt, to about 22 wt % rye malt, to about 24 wt % rye malt, to about 26 wt % rye malt, to about 28 wt % rye malt, or any amount therebetween. Embodiments featuring barley or barley malt may include about 2 wt % barley malt up to about 4 wt % barley malt, to about 6 wt % barley malt, to about 8 wt % barley malt, to about 10 wt % barley malt, to about 12 wt % barley malt, to about 14 wt % barley malt, to about 16 wt % barley malt, to about 18 wt % barley malt, to about 20 wt % barley malt, or any amount therebetween.

One or more components of the mash may be pressed and/or milled prior to or after mixing with one or more other mash components. A roller and/or hammer mill may be used to grind mash components, such as grain. After one or more pre-processing steps, the mash components may be added to a vessel, e.g., a mash tun, where the components may be agitated and heated.

Fermentation—The treated mash mix may be fermented via yeast-driven conversion of the sugars present in the mash into alcohol. Fermentation may be conducted in a large fermentation tank or vessel, into which the mash mix may be deposited. In particular embodiments, yeast may be admixed with the mash mix (filtered or unfiltered) and fermentation allowed to occur for up to about 15 days, or until about 1% to about 20% ethanol is produced. The final ethanol concentration of the fermentate may range from about 1% up to about 20%, or any percentage therebetween, such as up to about 2%, to about 3%, to about 4%, to about 5%, to about 6%, to about 7%, to about 8%, to about 9%, to about 10%, to about 11%, to about 12%, to about 13%, to about 14%, to about 15%, to about 16%, to about 17%, to about 18%, to about 19%, or more.

The production of compounds driving or contributing to beverage harshness, e.g., C2-C10 aliphatic aldehydes, may occur regardless of the fermentation organisms or sugar sources used to create the ethanol. The disclosed enzyme(s) may be added at various loading levels before, during, or after the commencement of fermentation to minimize or eliminate such compounds. An aldehyde dehydrogenase, for example, may be added at loading levels ranging from about 1 mg/L to about 2 g/L of fermentation volume, or any amount therebetween, including about 5 mg/L to about 2 g/L, about 50 mg/L, about 100 mg/L, about 150 mg/L, about 200 mg/L, about 250 mg/L, about 300 mg/L, about 350 mg/L, about 400 mg/L, about 450 mg/L, about 500 mg/L, about 550 mg/L, about 600 mg/L, about 650 mg/L, about 700 mg/L, about 750 mg/L, about 800 mg/L, about 850 mg/L, about 900 mg/L, about 950 mg/L, or more.

The timing of enzyme addition may be at any point before or during fermentation, or shortly thereafter, up to just before distillation, and for instance upon the formation of the mash, upon addition of yeast, or after partial fermentation such as to about 5 to about 10% completion, to about 20% completion, to about 30% completion, to about 40% completion, to about 50% completion, to about 60% completion, to about 70% completion, to about 80% completion, to about 90% completion, to about 95% completion, or to about 100% completion of the total alcohol production targeted as disclosed herein (e.g., up to about 20% ethanol). Alternatively, the disclosed enzyme may be added during fermentation with a residence time ranging from about 5 minutes to several days, including for example less than about 6 hours to about 6 hours, to about 12 hours, to about 36 hours, to about 48 hours, to about 60 hours, to about 72 hours, or longer. Enzyme addition may also occur after distillation but before or after bottling. Embodiments may also involve adding the enzyme(s) before fermentation. Additional embodiments may involve adding the enzyme(s) to the distilled ethanol within the aging barrels together with any ingredients desired for production of a particular beverage.

In some examples, one or more dinucleotide cofactors, such as NAD+ and/or NADP+, may also be added during the fermentation process at any of the aforementioned times or production stages. The cofactor(s) may be added at a loading level spanning about 0 mg/L to about 1 mg/L of fermentation volume, or up to about 2 g/L of fermentation volume, or any amount therebetween, including about 25 mg/L, 50 mg/L, about 100 mg/L, about 150 mg/L, about 200 mg/L, about 250 mg/L, about 300 mg/L, about 350 mg/L, about 400 mg/L, about 450 mg/L, about 500 mg/L, about 550 mg/L, about 600 mg/L, about 650 mg/L, about 700 mg/L, about 750 mg/L, about 800 mg/L, about 850 mg/L, about 900 mg/L, about 950 mg/L, or more. Embodiments featuring the use of both an aldehyde dehydrogenase and a cofactor may enhance or optimize the reduction in harshness. The combination of an aldehyde dehydrogenase and NAD+, for example, may enhance or maximize the reduction of harshness-causing compounds. In some embodiments, no extraneous cofactor may be added, and the effect of harshness reduction/elimination still equally achieved. Accordingly, the disclosed methods may be implemented via enzyme addition, with or without a cofactor. In some examples, the combination of an aldehyde dehydrogenase (e.g., Enzyme 2) and a cofactor comprising NAD+ may achieve optimal harshness reduction relative to other native enzymes when added to a fermentate with or without NAD+. The combination of an aldehyde dehydrogenase (e.g., Enzyme 3) and a cofactor comprising NADP+ may also exhibit significant harshness reduction relative to other native enzymes. Cofactor addition may be unnecessary in certain embodiments, for example those involving the use of an engineered enzyme, or those involving the use of an enzyme having an amino acid sequence at least about 80%, 85%, 90%, 95%, 99% or 100% identical to at least one native form of the enzyme, e.g., Enzyme 2 and/or Enzyme 3, having an amino acid sequence substantially similar or identical to SEQ ID NO: 6 and SEQ ID NO: 8, respectively.

The pH of the fermentate may be adjusted in some examples. For instance, a base compound, e.g., calcium carbonate, may be added at one or more points during fermentation to increase the pH of the fermentate to a range of about 5.0 to about 7.0, especially if a native enzyme is used. Specific embodiments may involve increasing the pH to about 6.0 to about 7.0, e.g., about 6.1, about 6.2, about 6.3, about 6.4, about 6.5, about 6.6, about 6.7, about 6.8, or about 6.9. In some examples, pH adjustment may be unnecessary, for example if an engineered enzyme is used or the native enzyme has activity within the required ranges. According to those embodiments, the pH of the fermentate may range from about 3.0 to 6.0.

The temperature of the fermentate may also vary, ranging in some examples from about 15° C. (59° F.) to about 37° C. (98.6° F.), or any temperature therebetween, for example about 17° C. (62.6° F.), 19° C. (66.2° F.), 21° C.(69.8° F.), 23° C. (73.4° F.), 25° C. (77° F.), 27° C. (80.6° F.), 29° ° C. (84.2° F.), 31° C. (87.8° F.), 33° C.(91.4° F.), 35° C.(95° F.), or higher. The temperature may be maintained at a constant or substantially constant level for all or most of the fermentation cycle.

In some embodiments, the temperature may vary one or more times over the course of fermentation. According to such embodiments, the temperature may be maintained within a range spanning about 15° C. (59° F.) to about 37° C. (98.6° F.) for at least about 50% to about 100% of the fermentation time, or to about 55% of the fermentation time, to about 60% of the fermentation time, to about 65% of the fermentation time, to about 70% of the fermentation time, to about 75% of the fermentation time, to about 80% of the fermentation time, to about 85% of the fermentation time, to about 90% of the fermentation time, to about 95% of the fermentation time, or longer.

Fermentation may be conducted under a variety of pressures. In some embodiments, fermentation may be conducted at pressures ranging from about 5 psi to about 20 psi, or to about 6 psi, to about 7 psi, to about 8 psi, to about 9 psi, to about 10 psi, to about 11 psi, to about 12 psi, to about 13 psi, to about 14 psi, to about 15 psi, to about 16 psi, to about 17 psi, to about 18 psi, to about 19 psi, or greater, or any pressure therebetween.

The resulting mixture may be fermented up to or about 10 days in the presence of *Saccharomyces cerevisiae*. In some embodiments, the enzyme may be added to the mixture, and remain active therein, for at least about 5 minutes up to at least about 5 days, or any length therebetween or beyond, e.g., up to about 1 day, to about 2 days, to about 3 days, to about 4 days, to about 6 days, to about 7 days, to about 8 days, to about 9 days, or longer. After fermentation, the fermentate may have an ethanol content ranging from about 1% to about 20%, or any concentration therebetween, including about 2%, 4%, 6%, 8%, 10%, 12%, 14%, 16%, 18%, or more.

Distillation—Once fermentation is complete, a distillation process may be implemented to obtain an ethanol concentration approximately equal to or greater than 10% ABV, for example. In some embodiments, the fermentate (filtered or unfiltered) may be heated in batch-wise or continuous fashion in accordance with the desired distillation process (except for non-distilled beverages (e.g., beer, wine, etc.)) which may be subjected to one or more post-fermentation processes that do not involve distillation). Heating of the fermentate may be performed in a still apparatus, such as a pot still. Heating may cause the ethanol present within the fermentate to vaporize, thus separating it from the unwanted grain particles, liquids, etc. present in the fermentate. The ethanol vapor may then be condensed via cooling in a condenser and subsequently collected in a collection apparatus. In some examples, the still apparatus, condenser and/or collection apparatus may be included in a single, unitary apparatus, which may be referred to as the still in some examples.

The fermented liquid may be distilled to an ethanol concentration of about 20% to about 95%. The dehydrogenase may not be passed through distillation, instead remaining in the portion of distillation liquid that is not collected as a consumable alcoholic beverage.

Bottling/Aging—The distilled ethanol may be diluted to any desired concentration and bottled or poured into wooden barrels for additional aging. After the desired aging period is complete, the liquid in the barrels may be adjusted to reach the desired ethanol concentration, then bottled for distribution. In some embodiments, one or more dehydrogenases may be added to the distilled ethanol after bottling and/or barreling, such that the harshness-causing aldehyde content is reduced directly in the bottles/barrels before consumption. According to such embodiments, the dehydrogenase(s) may be added at various loading levels ranging from about 5 mg/L to about 2 g/L of distilled alcohol volume, or any amount therebetween, including about 50 mg/L, about 100 mg/L, about 150 mg/L, about 200 mg/L, about 250 mg/L, about 300 mg/L, about 350 mg/L, about 400 mg/L, about 450 mg/L, about 500 mg/L, about 550 mg/L, about 600 mg/L, about 650 mg/L, about 700 mg/L, about 750 mg/L, about 800 mg/L, about 850 mg/L, about 900 mg/L, about 950 mg/L, or more.

The final ethanol concentration of the distilled alcoholic beverage may range from about 10% to about 70%, or to about 15%, to about 20%, to about 25%, to about 30%, to about 35%, to about 40%, to about 45%, to about 50%, to about 55%, to about 60%, to about 65%, to about 70%, to about 75%, to about 80%, to about 85%, to about 90%, to about 95%, or greater. In some examples, the ethanol concentration may be subsequently diluted for consumption, such that the final concentration drops below 10%, e.g., about 1%, about 2%, about 3%, about 4%, about 5%, about 6%, about 7%, about 8%, about 9%, or any level therebetween.

As provided, the disclosed enzyme(s) may be added at any point before or during fermentation or shortly thereafter, up to just before distillation, with the disclosed residence time ranges, and/or may involve adding the enzyme to the distilled ethanol within the aging barrels together with any ingredients desired for production of a particular beverage. Some embodiments may also involve adding the enzyme(s) before fermentation. Moreover, given the previous difficulty associated with pinpointing an effective mechanism for delivering the enzyme(s), the discovery that adding the enzyme(s) to the fermentate or distillate during the beverage production process was surprising.

Beverage Products

Beverages produced via the aforementioned methods may have a reduced aldehyde content relative to an identically formulated and processed beverage, but for the enzymatic treatment disclosed herein, including the enzyme(s) type, timing of enzyme addition, and concentration of enzyme addition, all of which may be critical to the effective oxidation of the carbonyl groups present on the targeted compounds. Embodiments of the beverage may specifically have a reduced amount of aliphatic, electrophilic aldehydes, which may include or comprise C2-C10 aliphatic aldehydes, relative to beverages not treated with enzyme(s) in accordance with the approaches disclosed herein.

Experimental Examples

A series of experiments was performed to demonstrate the effectiveness of aldehyde dehydrogenases to effectively oxidize harshness-causing compounds under conditions often applied during the production of consumable alcoholic products. Additional experiments were performed to confirm the effectiveness of aldehyde dehydrogenases to effectively oxidize harshness causing compounds during the production of consumable alcoholic products. Taste-testing was also conducted to verify the harshness reduction perceived by users upon consuming consumable alcoholic products produced via implementation of the methods disclosed herein. As noted below, certain aldehyde dehydrogenases were selected for initial evaluation and continued testing for exemplary purposes, only. It should thus be understood that the harshness-reducing effect disclosed herein is not limited to that achieved by using the specific enzymes tested in the experiments below, which include a subset of enzymes tested to demonstrate the effective oxidation of harshness-causing compounds under conditions often applied during distilled alcohol production, and the readily observable reduction in beverage harshness that results. Enzymes similar or identical at least to any one of SEQ ID NOS: 1-17, including all or substantially all aldehyde dehydrogenases, may be effective under conditions similar to those applied below.

Experiment 1—Aldehyde Dehydrogenase Screen and Activity Assessment

Experiment 1 was performed to demonstrate that dehydrogenase enzymes from different sources effectively target compounds responsible for harshness. In particular, a spectrophotometric assay was performed to determine the activity of 15 different aldehyde dehydrogenases (corresponding to SEQ ID NOS: 1-15) in the presence of multiple aldehyde substrates. The source organisms of the enzymes varied, indicating that a variety of enzymes derived from a variety of sources may be effective to achieve the results disclosed herein. Human-derived aldehyde dehydrogenases were tested, for instance, as well as enzymes derived from *Bacillus, E. Coli*, macaca Fascicularis, otolemur garnettii, Pteropus alecto, *Geobacillus*, Parageobacillus caldoxylosilyticus, *Citrobacter rodentium, Shigella boydii, Klebsiella pneumonia*, and *Acinetobacter*.

Figure 2:
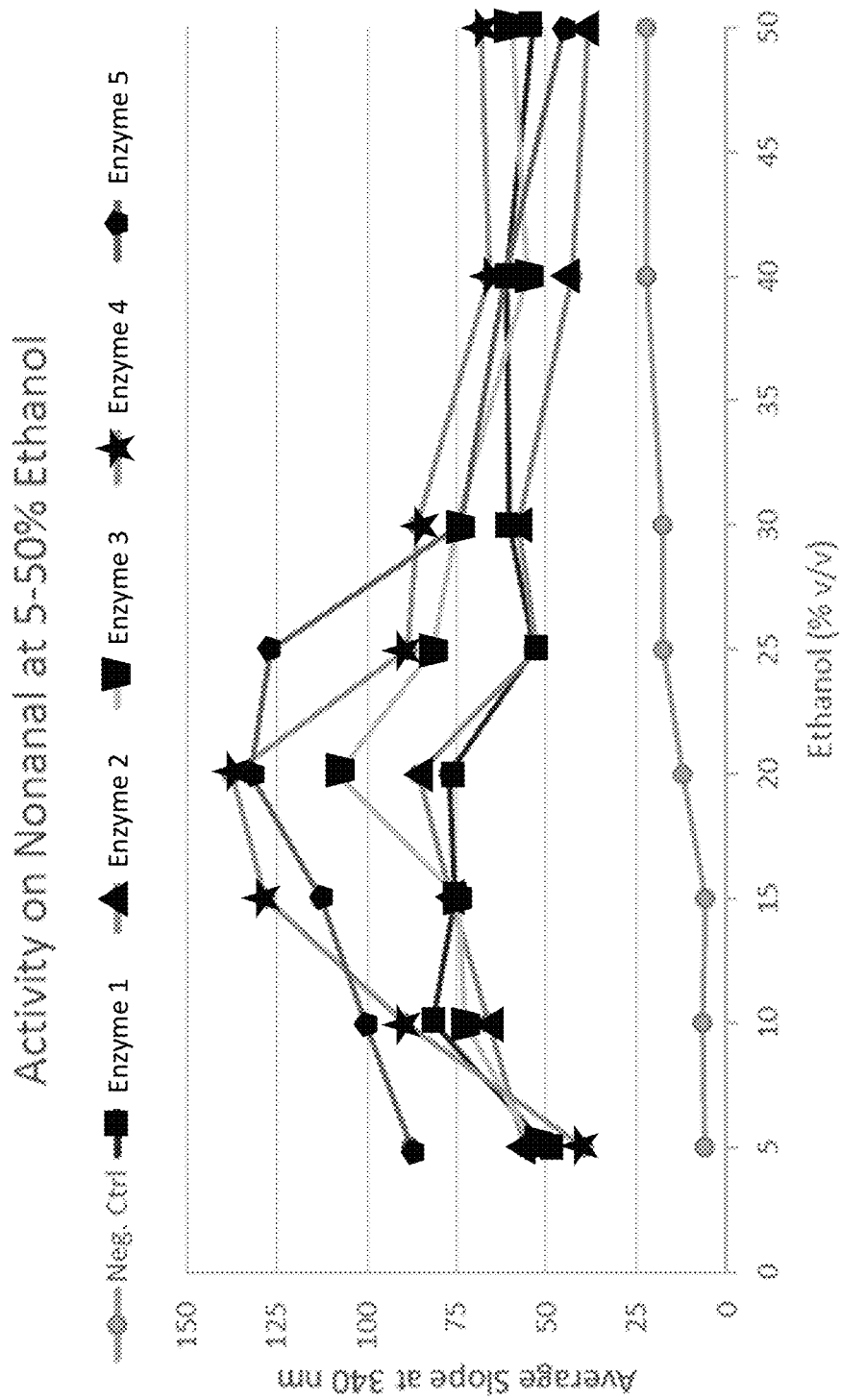
FIG. 2 is a graph showing the activity levels of the aldehyde dehydrogenases represented in FIG. 1 in the presence of nonanal in accordance with embodiments of the present disclosure.

Enzyme activity was measured by the conversion of NADP+ to NAD(P)H, as aldehyde dehydrogenase activity is dependent on NAD(P)+. Because NAD(P)H absorbs light at 340 nm and NAD(P)+ does not, NAD(P)H generation was monitored via spectrophotometry at 340 nm for 10 minutes in the presence of an equimolar amount of NAD(P)+ and five different aldehyde substrates, which included acetaldehyde, crotonaldehyde, n-octanal, n-nonanal, and n-dodecanal, each of which was provided at 5 mM (220-292 ppm) and 0.5 mM (22-92 ppm) in separate samples.

Where all aldehyde dehydrogenases will act on aldehydes, the objective of the experiment was to select the most active under specific conditions. Of the 15 enzymes, the five that showed the highest activity with all substrates at 500 µM, specifically, (identified as Enzymes 1-5, corresponding respectively to SEQ ID NOS: 5, 6, 8, 14, and 15) were subjected to additional evaluation, starting with an assessment of the enzymes' tolerance to ethanol concentrations typically present during fermentation and distillation processes. First, each enzyme was screened against 5 mM acetaldehyde and 5 mM n-nonanal at ethanol concentrations ranging from 5% v/v to 50% v/v ethanol. As shown respectively in FIGS. 1 and 2, the activity of each enzyme remained relatively stable in the presence of acetaldehyde and n-nonanal up to about 20-30% v/v ethanol, at which point the activity levels generally dropped. This demonstrates that numerous aldehyde dehydrogenases, even when derived from distinct source organisms, effectively act on and catalyze aldehydes responsible for the harsh bite associated with alcohol. Additional dehydrogenases, including but not limited to the 15 tested in the experiment, may also effectively act on and catalyze aldehydes responsible the harshness typically associated with consumable beverages and components thereof.

Figure 3:
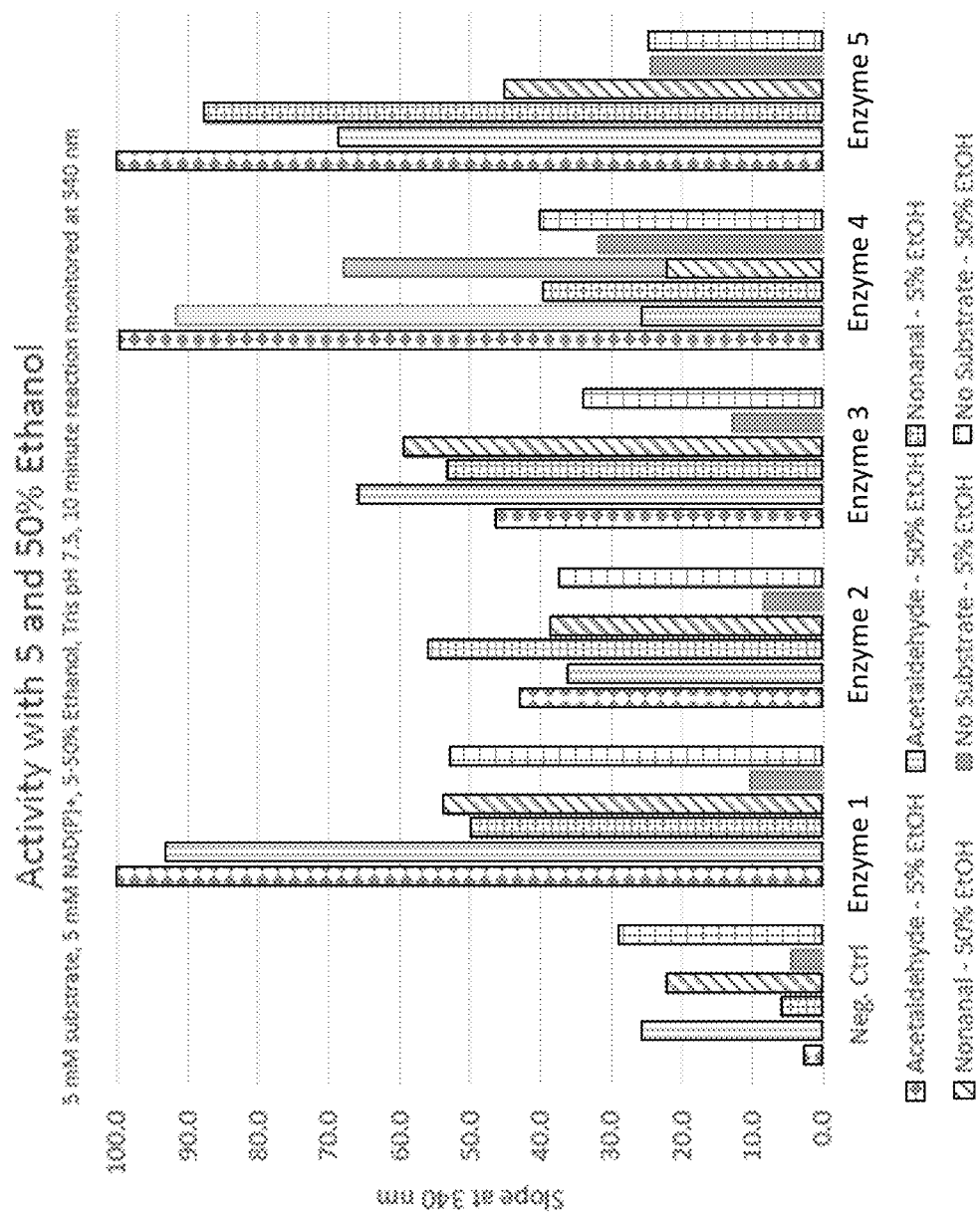
FIG. 3 is a graph showing the activity levels of the aldehyde dehydrogenases in the presence of acetaldehyde and nonanal at different ethanol concentrations in accordance with embodiments of the present disclosure.

The activity of each enzyme was also evaluated with and without available substrates (acetaldehyde and nonanal) in 5% v/v ethanol and 50% v/v ethanol to further elucidate the enzymes' ethanol tolerance and identify any background enzymatic activity. The results shown graphically in FIG. 3 illustrate that each enzyme did exhibit equal or greater activity at 50% v/v ethanol without the presence of a substrate than at 5% v/v. The results further showed, however, that each enzyme exhibited increased activity in the presence of acetaldehyde and nonanal relative to the activity measured in the absence of an aldehyde substrate.

Figure 4:
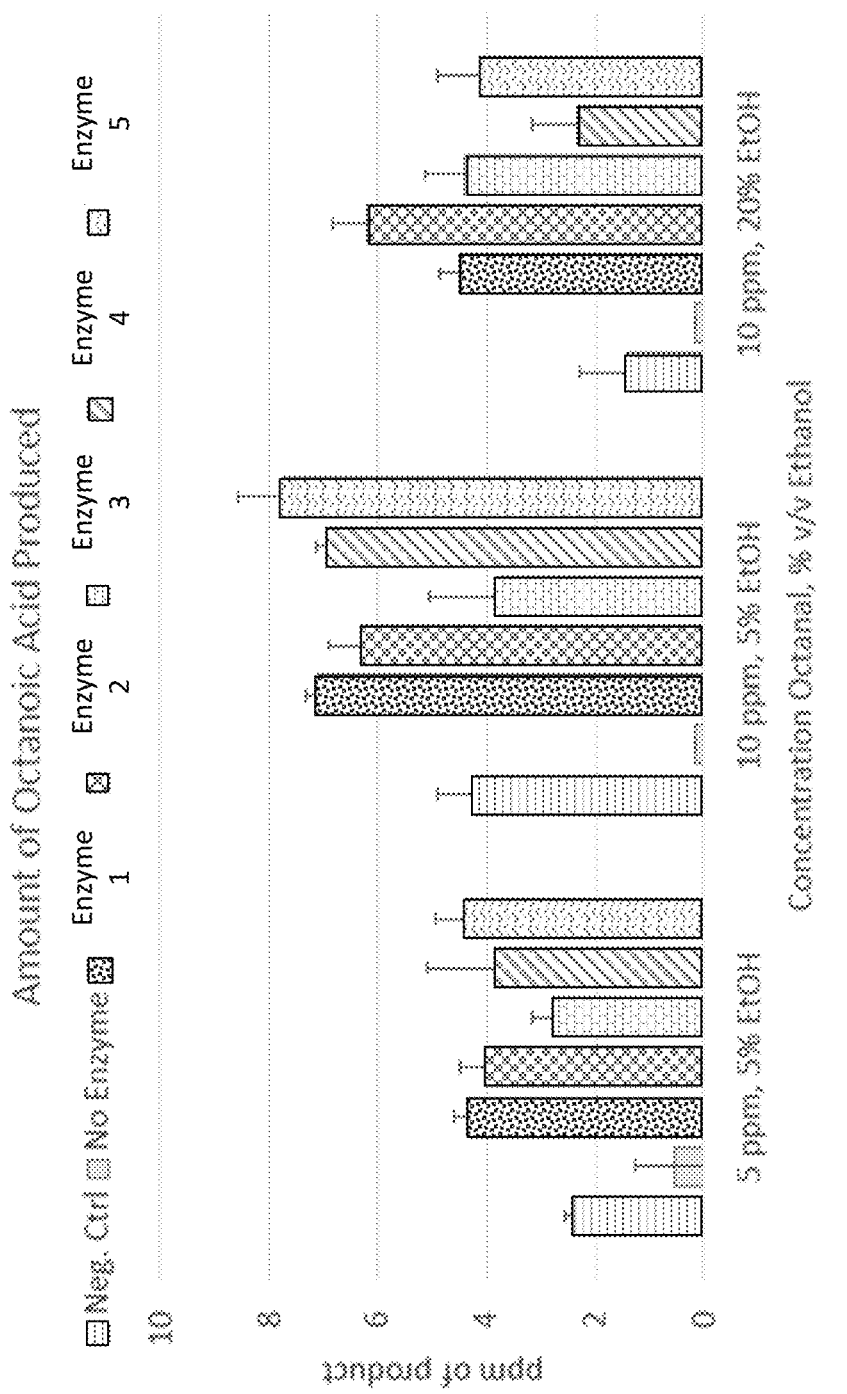
FIG. 4 is a graph showing the activity levels of the aldehyde dehydrogenases at different ethanol concentrations determined based on the amount of octanoic acid produced in accordance with embodiments of the present disclosure.
Figure 5:
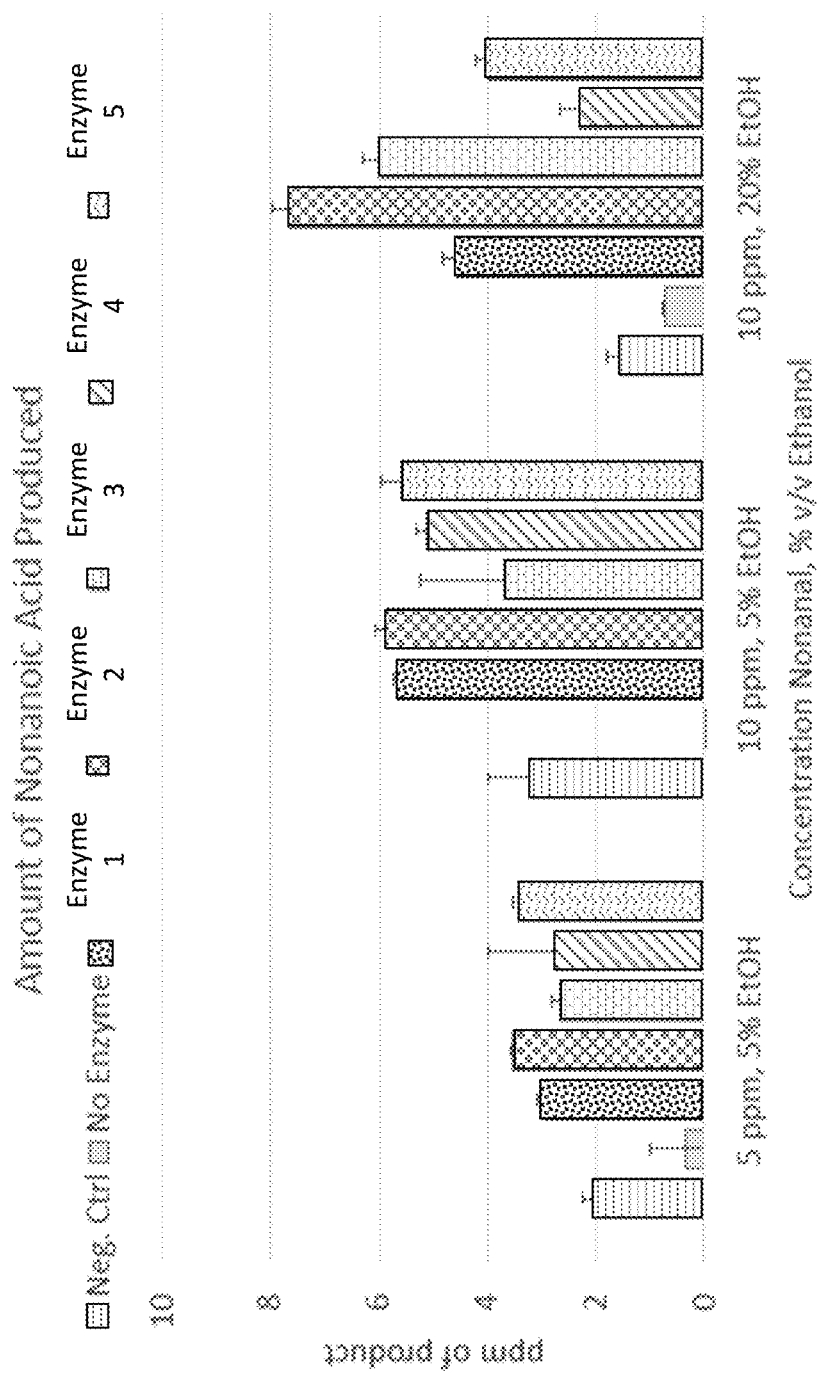
FIG. 5 is a graph showing the activity levels of the aldehyde dehydrogenases at different ethanol concentrations determined based on the amount of nonanoic acid produced in accordance with embodiments of the present disclosure.
Figure 6:
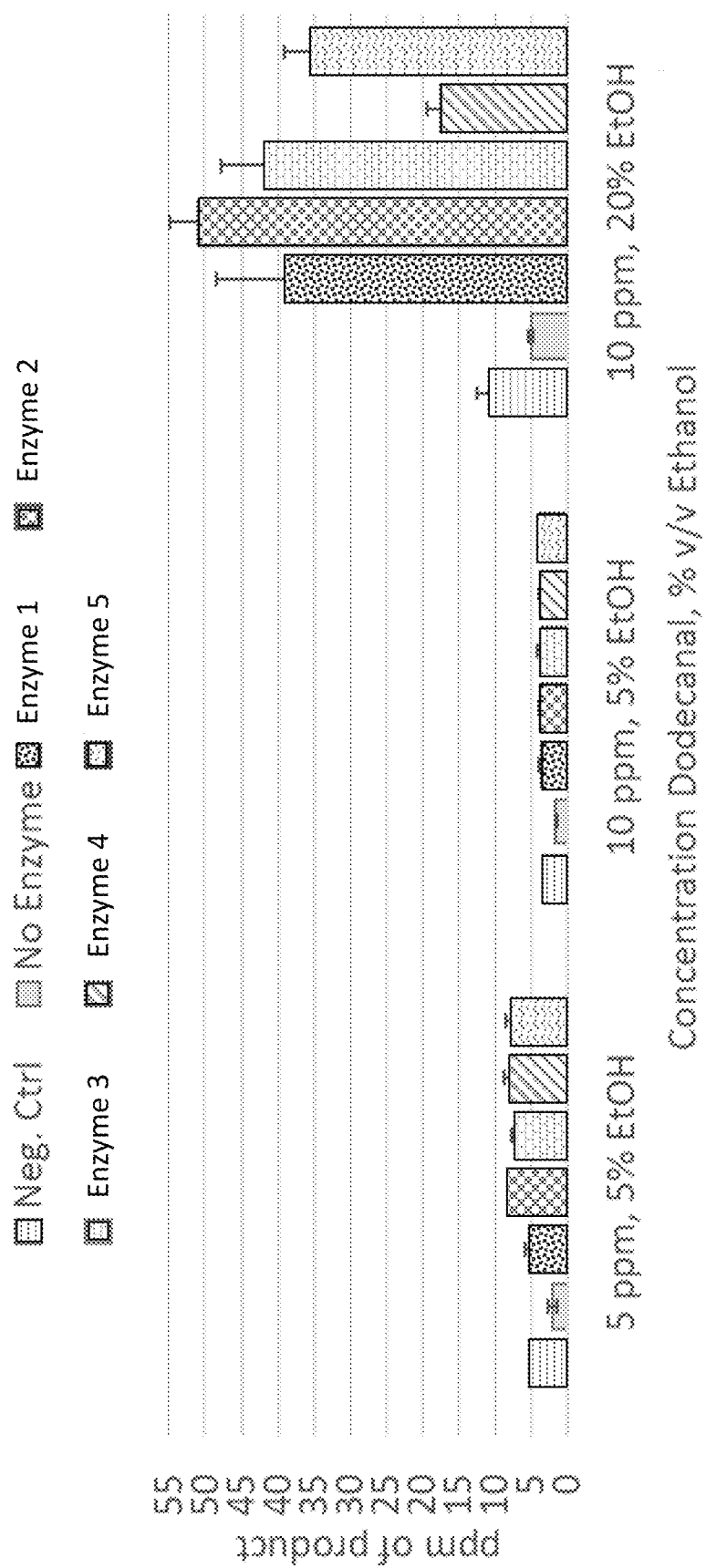
FIG. 6 is a graph showing the activity levels of the aldehyde dehydrogenases at different ethanol concentrations determined based on the amount of dodecanoic acid produced in accordance with embodiments of the present disclosure.

The activity of each enzyme in the presence of low substrate concentrations was further evaluated via gas chromatography. To learn more about the enzymes' ethanol tolerance, each enzyme was also tested in the presence of 10 ppm n-octanal, n-nonanal, and n-dodecanal in 20% v/v. Based on the amount of octanoic acid produced, shown graphically in FIG. 4, all enzymes exhibited activity in the presence of octanal at 10 ppm or lower. As shown in FIG. 5, all enzymes also showed activity in the presence of 5 ppm and 10 ppm nonanal, with Enzyme 2 again maintaining high activity levels at each substrate concentration at both 5% v/v and 20% v/v ethanol. The results shown in FIG. 6 illustrate that all enzymes exhibited appreciable activity at 5 ppm and 10 ppm dodecanal in both 5% v/v and 20% v/v ethanol. Enzyme 2 showed the highest activity at both 5 ppm, 5% v/v ethanol and 10 ppm, 20% v/v ethanol.

The spectrophotometric and gas chromatographic screens showed that Enzyme 2 exhibited strong ethanol tolerance evidenced by the absence of activity decline at 20% v/v ethanol. Enzyme 2 also showed high activity levels in the presence of only 5-10 ppm of multiple aldehyde substrates. Together, these results indicate that one or more of the enzymes evaluated, including all of the enzymes, may function effectively in conditions relevant to alcoholic beverage production, e.g., distilled alcohol production, with Enzyme 2 exhibiting the highest activity in the specific experiments performed.

Experiment 2—Aldehyde Dehydrogenase Characterization.

Figure 7:
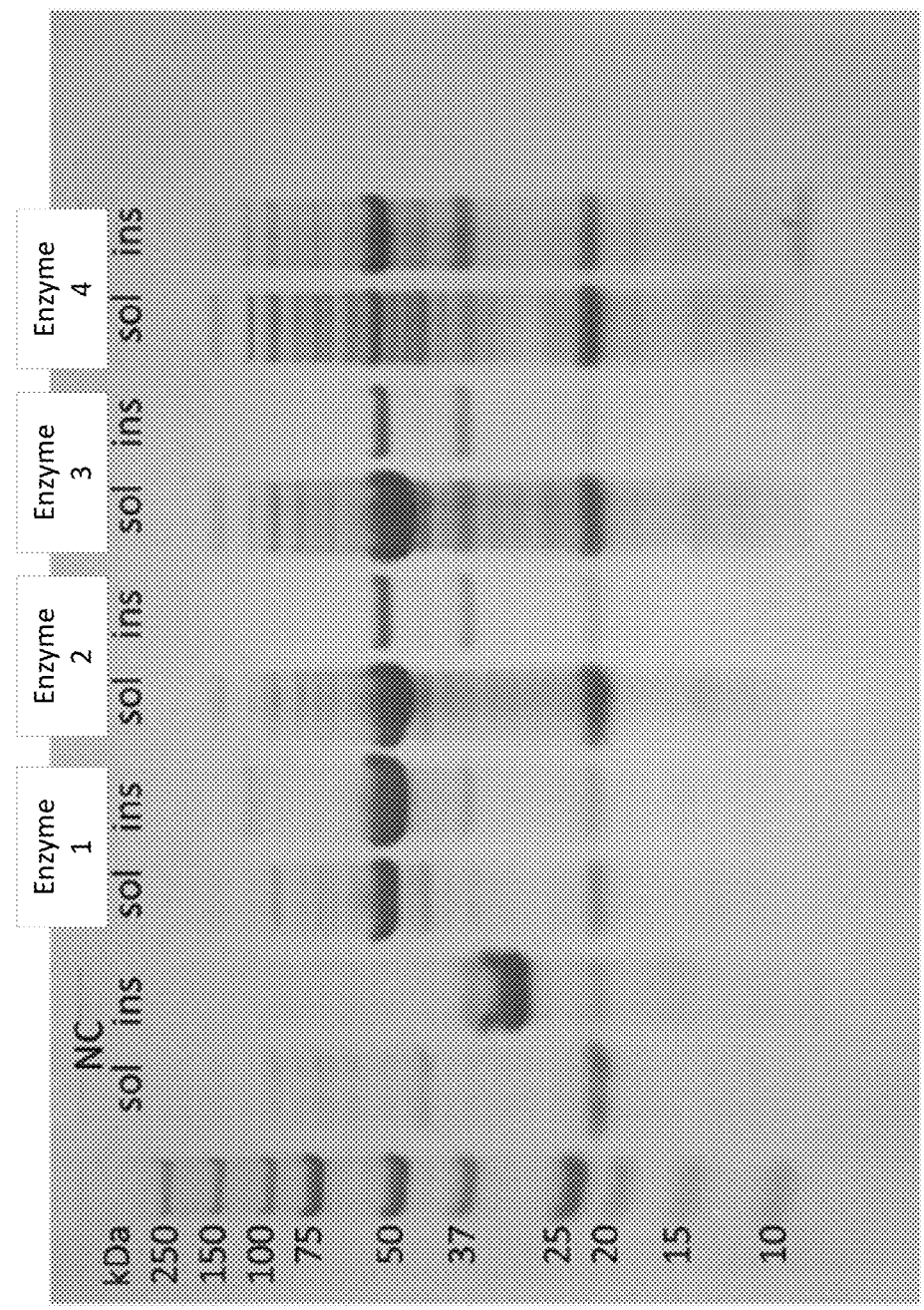
FIG. 7 is a Western blot showing the soluble and insoluble levels of four of the aldehyde dehydrogenase in accordance with embodiments of the present disclosure.

Experiment 2 was performed to select a specific enzyme for additional testing in a craft distillery to demonstrate the positive sensory impact of removing beverage harshness. Enzyme powder was produced for Enzymes 1~4 (corresponding to SEQ ID NOS: 5, 6, 8, and 14, respectively) concurrently with a negative control, and the relative amount of soluble versus insoluble powder determined. As shown in the Western blot of FIG. 7, Enzyme 2 (54.1 kDa) and Enzyme 3 (54.0 kDa) produced the highest relative levels of soluble protein. Based on the higher relative amount of soluble protein present in the powder, Enzymes 2 and 3 may function most effectively when added in powder form to substantially liquid fermentate and/or distillate samples.

Figure 8:
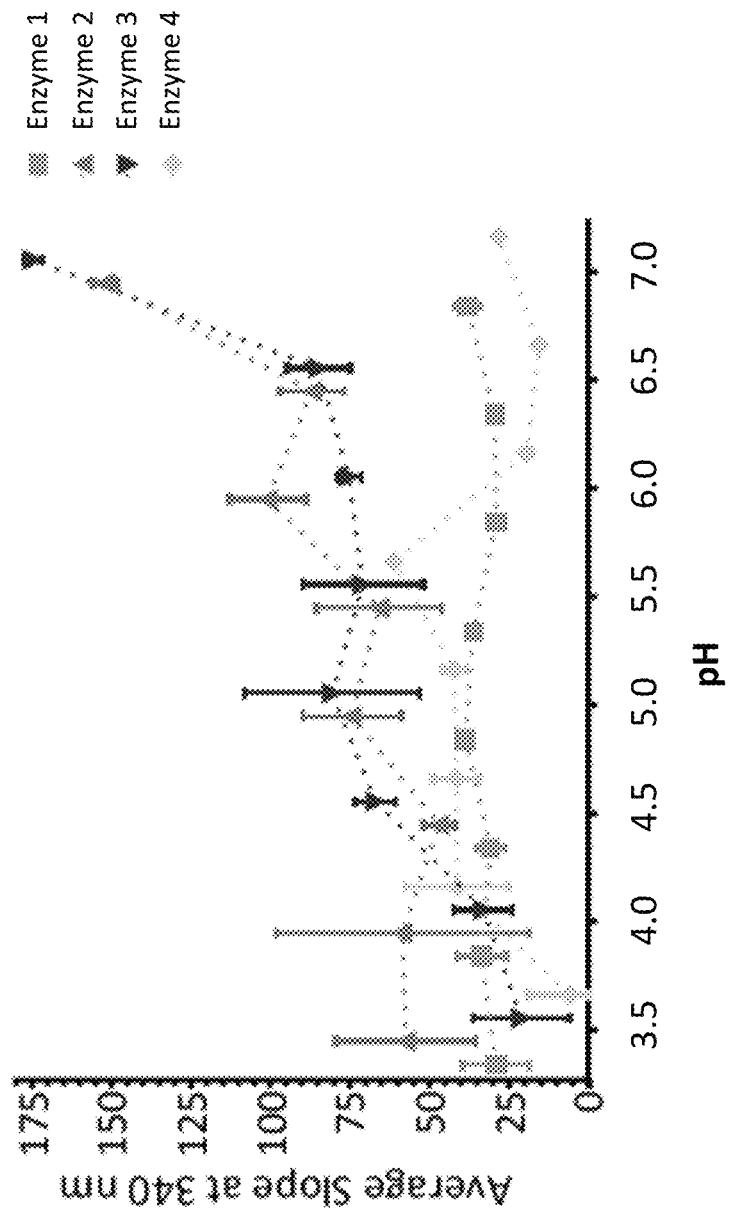
FIG. 8 is a graph showing the activity levels of the four aldehyde dehydrogenases represented in FIG. 7 at a range of pH values in 15% ethanol in accordance with embodiments of the present disclosure.
Figure 9:
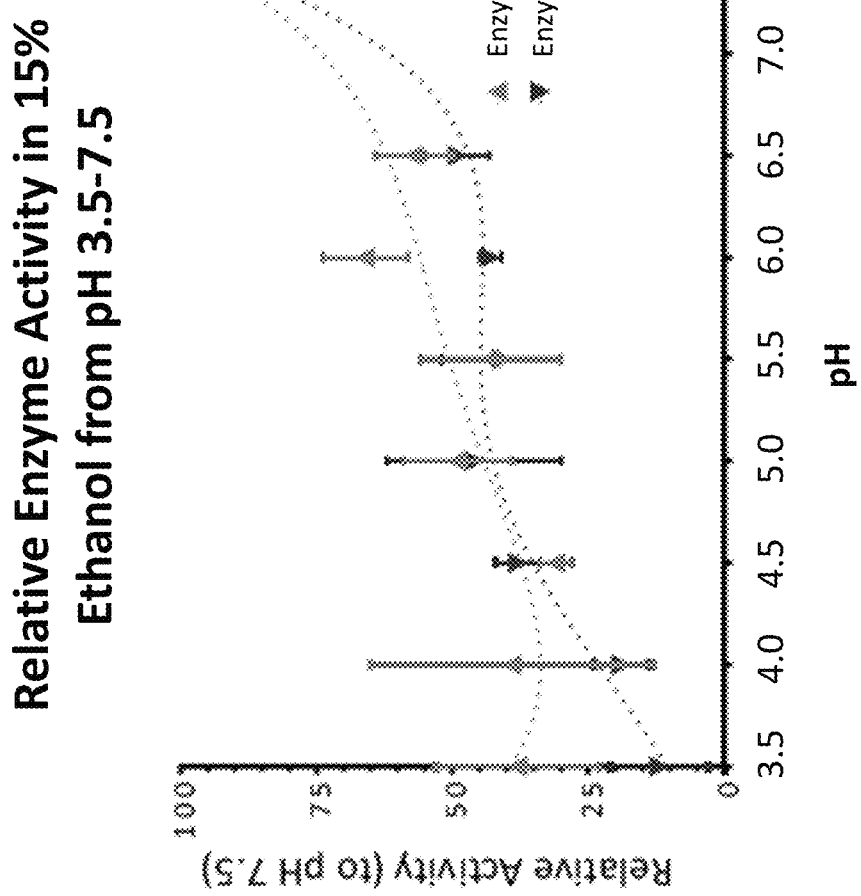
FIG. 9 is a graph showing the relative activity levels of two of the aldehyde dehydrogenases represented in FIG. 8 at a range of pH values in 15% ethanol in accordance with embodiments of the present disclosure.

The activity levels of Enzymes 1~4 were then assessed via the NAD(P)H spectrophotometric assay described above at pH levels ranging from 3.5 to 7.5 in 10% v/v and 15% v/v ethanol to assess the enzymes' function at elevated alcohol contents and reduced pH levels often applied during fermentation. FIG. 8 shows that Enzymes 1 and 4 exhibited less overall activity in 15% v/v ethanol across all pH values relative to Enzymes 2 and 3, which were the most stable of the enzymes at lower pH levels. FIG. 9 shows that Enzyme 2 was more stable than Enzyme 3 at most pH levels in 15% v/v ethanol, especially at pH values of 3.5 and 4.0.

Figure 10:
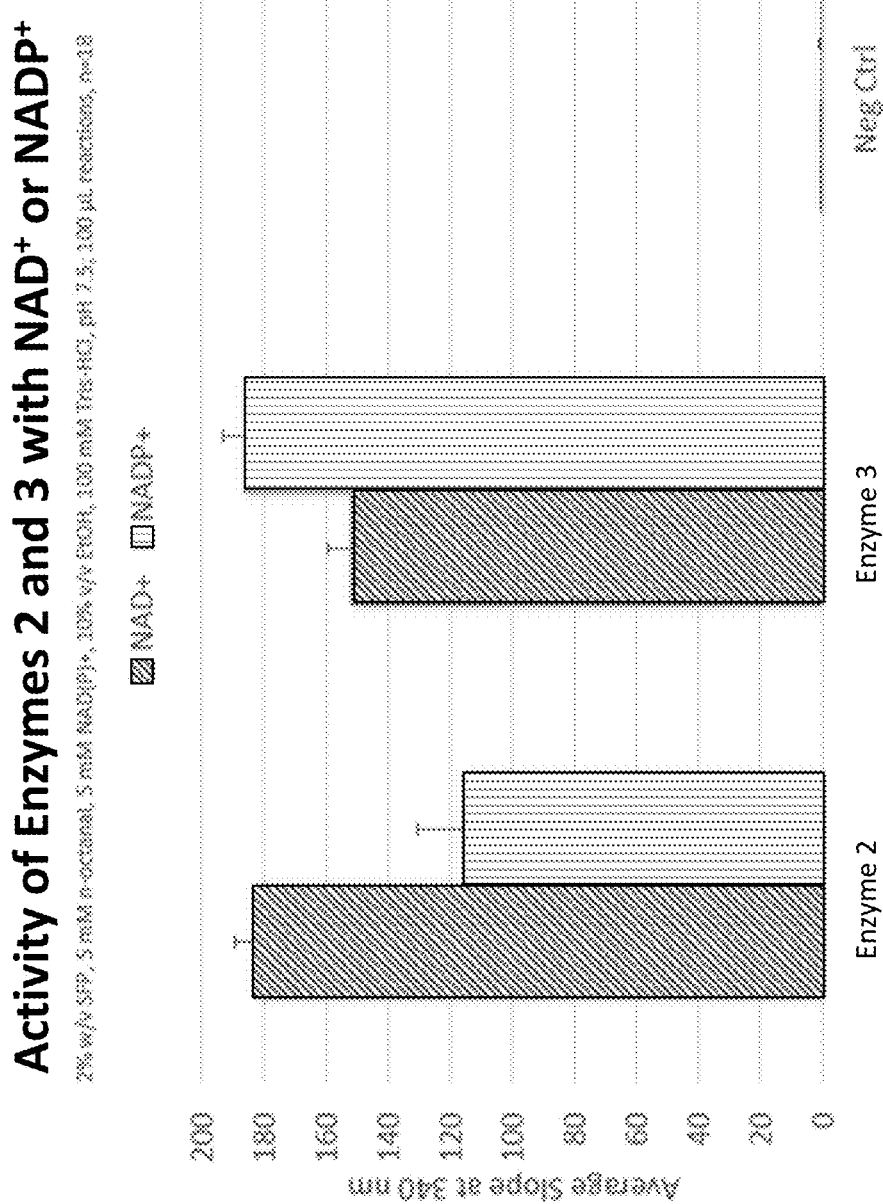
FIG. 10 is a graph showing the activity levels of the two aldehyde dehydrogenases with associated cofactors in the presence of n-nonanal in accordance with embodiments of the present disclosure.

Enzymes 2 and 3 were evaluated for NAD+ and NADP+ cofactor preference using the NAD(P)H spectrophotometric assay. As shown in FIG. 10, both enzymes demonstrated activity with both cofactors, with Enzyme 2 demonstrating about 1.5 times greater activity than Enzyme 3 with NAD+, and Enzyme 3 demonstrating about 1.2 times greater activity with NADP+. Accordingly, Enzyme 2 activity may be enhanced most significantly in the presence of NAD+, and Enzyme 3 activity may be enhanced most significantly in the presence of NADP+, even though both may be effective without the presence of a cofactor, including NAD+ and NADP+.

Enzymes 2 and 3 were further evaluated head-to-head, this time in the presence of 100 ppm octanal, nonanal, or dodecanal at pH 5.5 in 15% ethanol, at both 30° ° C. and 37° C. Each enzyme was tested at concentrations ranging from 0.001 g/L to 11 g/L of enzyme powder (1:100000-1:10 molar ratio enzyme:aldehyde). The activity level of each enzyme was measured at 1 hour, 4 hours, and 21 hours. NAD+ was used as a cofactor for Enzyme 2, and NADP+ was used as a cofactor for Enzyme 3. Reactions were quenched and extracted with ethyl acetate and assessed using gas chromatography, with substrate conversion determined by dividing the peak area product by the sum of the peak area product and peak area substrate.

Figure 11:
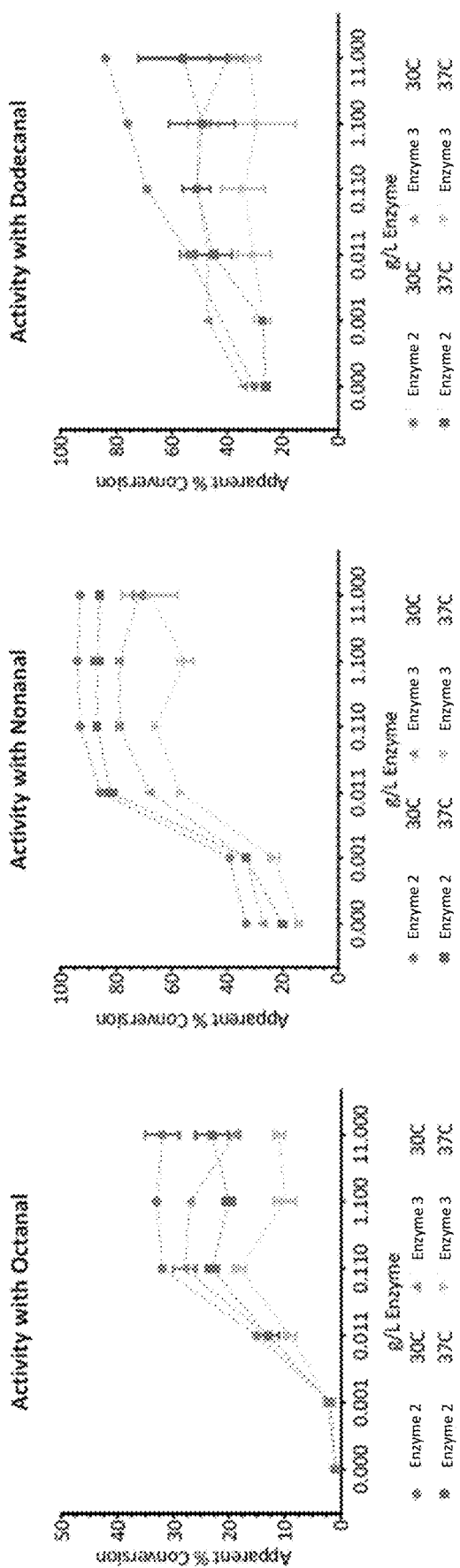
FIG. 11 provides three graphs collectively showing the activity levels of the two aldehyde dehydrogenases after four hours in the presence of octanal, nonanal, and dodecanal at 30° C. and 37° C. in accordance with embodiments of the present disclosure.
Figure 12:
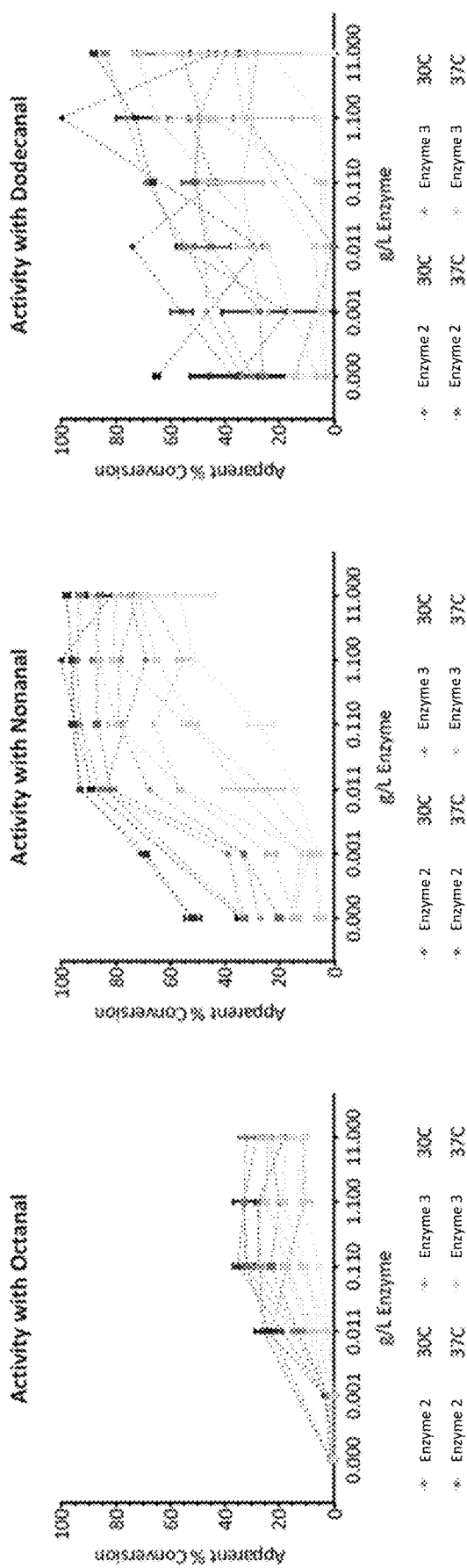
FIG. 12 provides three graphs collectively showing the activity levels of the two aldehyde dehydrogenases after 21 hours in the presence of octanal, nonanal, and dodecanal at 30° C. and 37° C. in accordance with embodiments of the present disclosure.

As shown in FIG. 11, Enzyme 2 showed the highest activity level relative to Enzyme 3 under all test conditions at the 4-hour time-point. Activity levels generally increased with increasing enzyme loading up to about 0.1 g/L enzyme, after which enzyme activities remained relatively constant. The highest activity level of Enzyme 2 was measured at pH 5.5, 15% v/v ethanol. FIG. 12 shows the activity levels of both enzymes at the 21-hour mark. As shown, activity levels for the enzymes were similar at 21 hours relative to 4 hours. Activity levels were higher for both enzymes at 30° C. than 37° C.

Accordingly, aldehyde dehydrogenases may effectively reduce the harshness of consumable beverages and beverage components, including one or more enzymes having an amino acid sequence similar or identical to any one of SEQ ID NOS: 1-17, such as Enzyme 2, corresponding to SEQ ID NO: 6. The aforementioned results further confirm that one or more of the enzymes evaluated, including all of the enzymes, may function effectively in conditions relevant to alcoholic beverage production, e.g., distilled alcohol production, with Enzyme 2 exhibiting the highest activity in the specific experiments performed.

Experiment 3—Enzyme 2 Distillation Analysis

When creating a distilled alcoholic beverage using a pot still, the first part of the distillate is generally discarded or otherwise not collected (the "heads"). After the heads have been discarded, the "heart" of the distillate is collected and used to create the beverage. Lastly, a portion of the distillation product composed of off-flavors, called the "tails," is often discarded as well.

In Experiment 3, the distillation heads, final 40% v/v ethanol product, and post-fermentation/pre-distillation samples obtained from distilled alcohol production processes disclosed herein were characterized with and without Enzyme 2 treatment using a gas chromatography—mass spectroscopy protocol. In particular, a control sample, a sample obtained after Enzyme 2 treatment, and a sample obtained after treatment with Enzyme 2 and NAD+ cofactor were obtained for each intermediary and final product of a fermentation/distillation process. Analyte peaks were identified for each sample to determine whether Enzyme 2 decreased the presence of potential harshness-causing compounds at one or more stages of the distilled alcohol production process.

Figure 13:
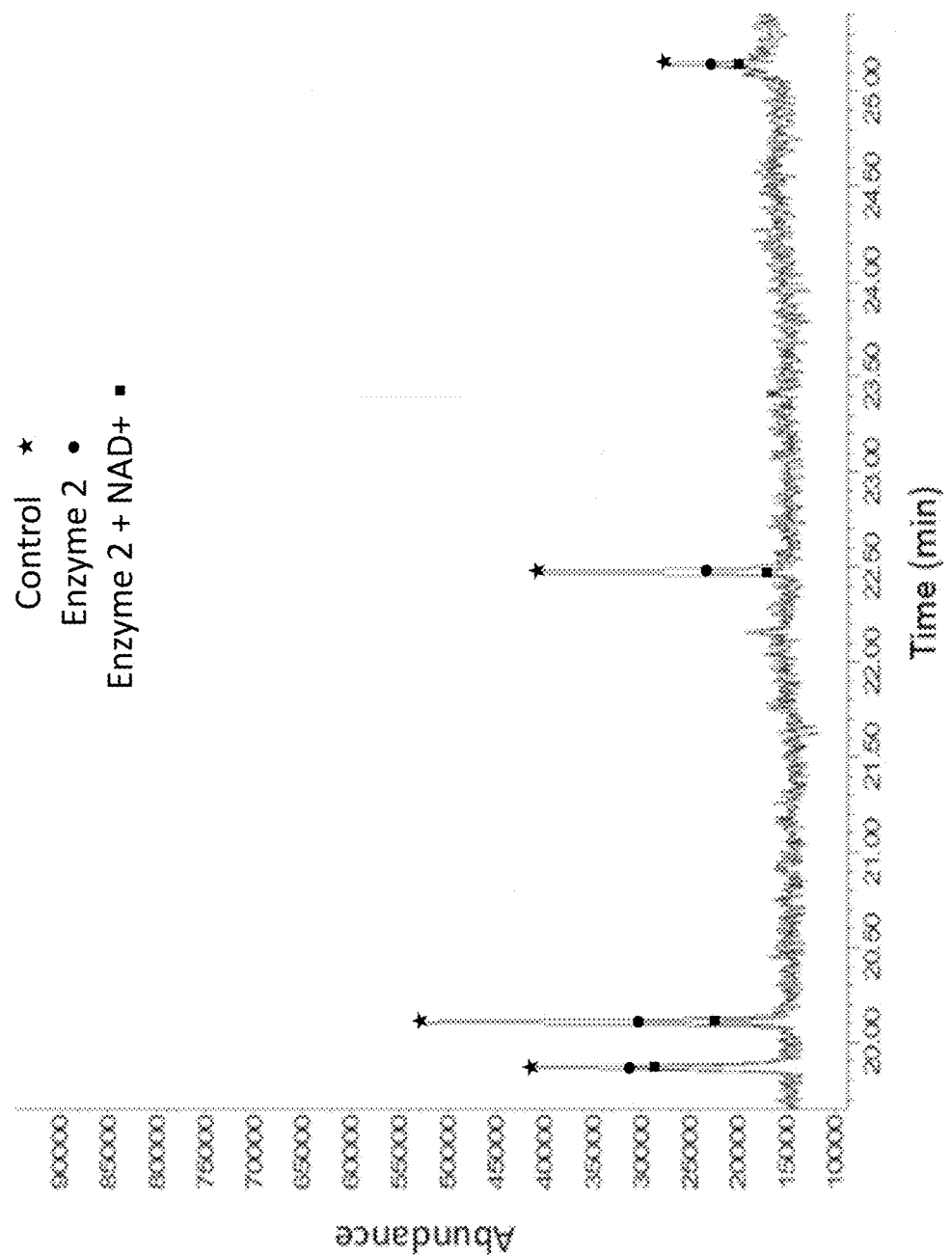
FIG. 13 is a mass spectrometry graph showing analyte abundance in 40% ethanol after treatment with one of the aldehyde dehydrogenases both with and without a cofactor in accordance with embodiments of the present disclosure.

FIG. 13 shows the analyte peaks identified in the 40% ethanol samples. The number and height of peaks were the highest in the control samples (labeled with stars), indicating a greater presence and amount of analytes in the samples not treated with the aldehyde dehydrogenase. The Enzyme 2-treated samples had smaller peaks than the control (labeled with circular dots), and the samples treated with Enzyme 2 and the NAD+ cofactor had the fewest peaks (labeled with squares), indicating that Enzyme 2 is effective when utilized together with the NAD+ cofactor.

Figure 14:
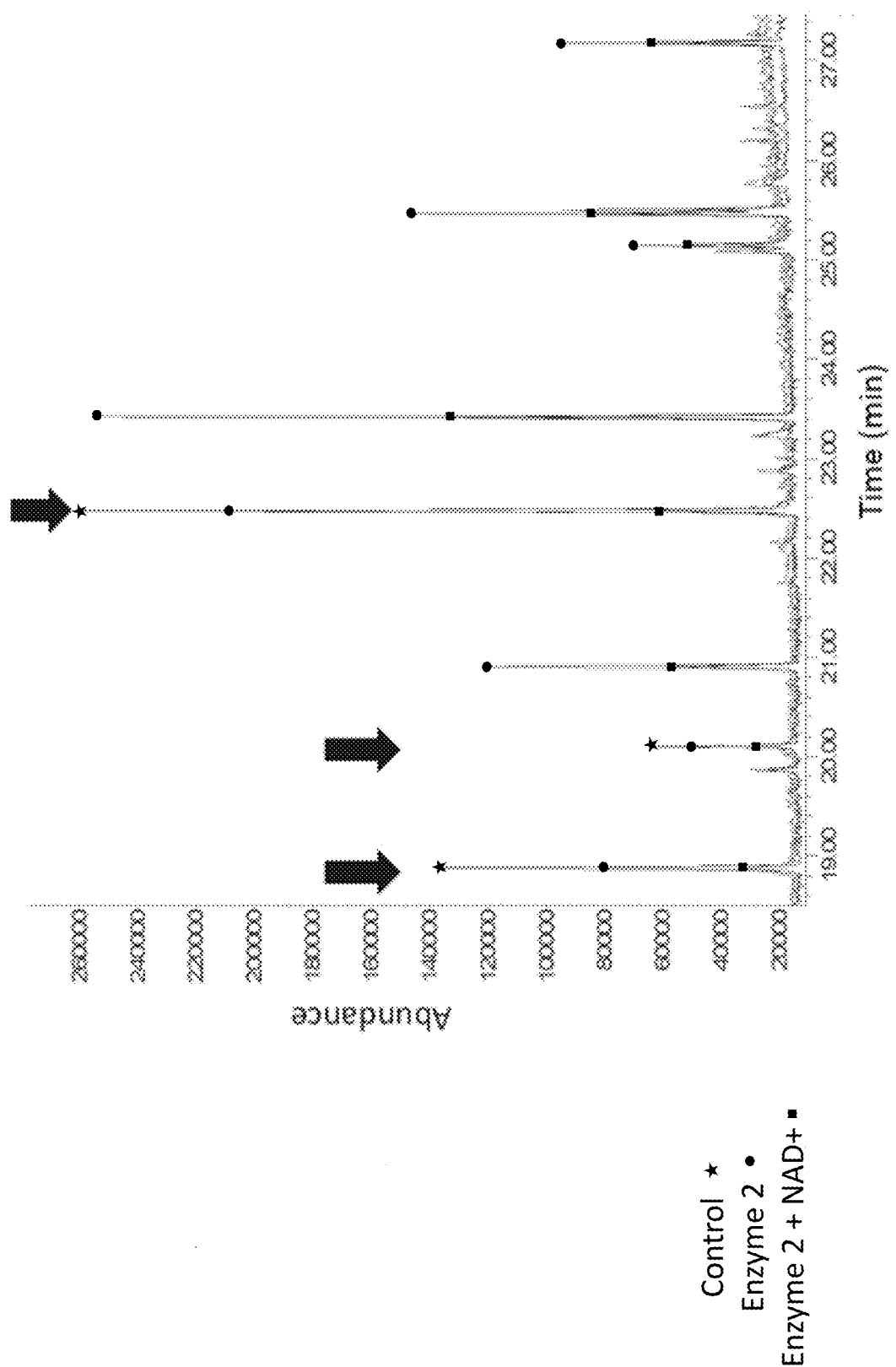
FIG. 14 is a mass spectrometry graph showing analyte abundance in heads samples after treatment with one of the aldehyde dehydrogenases both with and without a cofactor in accordance with embodiments of the present disclosure.

FIG. 14 shows the analyte peaks identified in the heads samples. The control samples showed the greatest number and height of peaks (labeled with stars). Samples treated with Enzyme 2 had visibly smaller peaks (labeled with circles), and samples treated with Enzyme 2 and the NAD+ cofactor again had the fewest peaks (labeled with squares), further indicating that Enzyme 2 may be the most effective in some examples when utilized together with the NAD+ cofactor, while Enzyme 2, alone, may also be effective, as may be any one of the aldehyde dehydrogenases at least about 80%, 85%, 90%, 95%, 99%, or 100% identical to any one of SEQ ID NOS: 1-17, or other aldehyde dehydrogenases.

Figure 15:
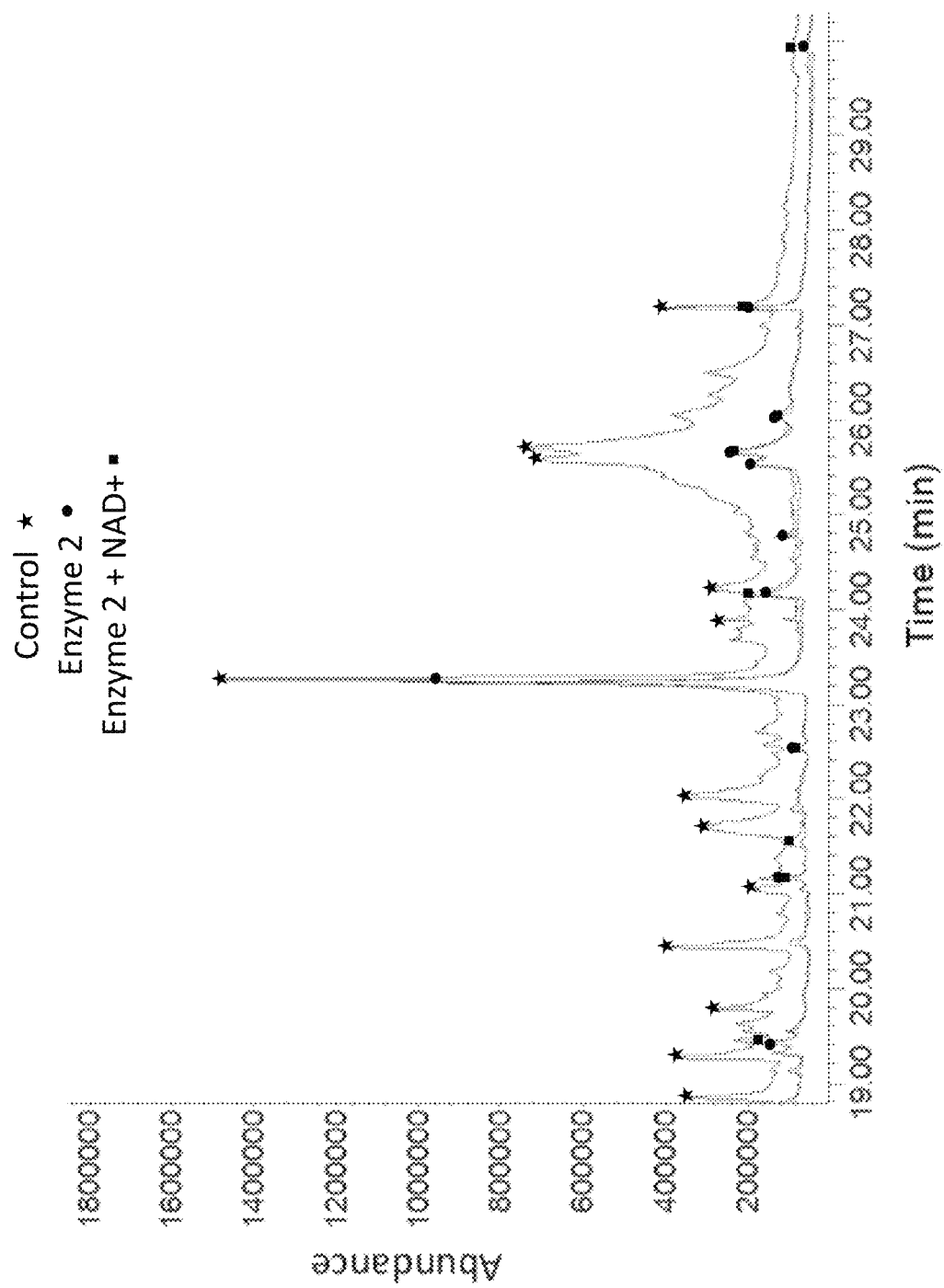
FIG. 15 is a mass spectrometry graph showing analyte abundance in fermentation samples after treatment with one of the aldehyde dehydrogenases both with and without a cofactor in accordance with embodiments of the present disclosure.

FIG. 15 shows the analyte peaks identified in the fermentation samples. As shown, more than five times as many peaks were identified overall, indicating the presence of a greater number of different analytes in the fermentate relative to the 40% ethanol and heads samples. Enzyme 2, both with and without NAD+(peaks labeled with circles and squares, respectively), reduced the number of peaks relative to the control (labeled with stars), further indicating that in a fermentate, Enzyme 2 may be effective with or without a cofactor, as may be any one of the aldehyde dehydrogenases at least about 80%, 85%, 90%, 95%, 99%, or 100% identical to any one of SEQ ID NOS: 1-17, or other aldehyde dehydrogenases, due at least to their common activity and homology.

Experiment 4—1$^{st}$ Distiller Trial with Enzyme 2; Testing an Un-Aged Whiskey

The ability of Enzyme 2 (with and without a cofactor) to act on multiple aldehydes present at very low levels at a unique range of pH and temperature was further evaluated in a distillation trial that produced sample whiskeys for tasting. This trial was performed at a commercial craft distillery. Effective oxidation of the targeted aldehydes by the aldehyde dehydrogenase was determined by collecting sensory data generated from test subjects after consuming distilled alcoholic beverages treated with the enzyme.

To produce the whiskey (a "White Dog" whiskey), a mash mix comprised of a blend of corn, rye malt, barley malt, and dextrin was formed and added to a 5.5 gallon fermenter. No acid was added. The starting temperature was 75° F. and the starting pH was 5.7. The mash was then fermented with brewer's yeast. About 24 and 48 hours after fermentation initiation, about 2.75 lbs. of a dextrose equivalent was added to the fermentate. The pH of the fermentate varied over the course of fermentation, measuring at about 3.5 after 48 hours, and after successive adjustments via teaspoon-wise calcium carbonate addition, measuring at a final pH of 6.7. This is a common ingredient used by distiller and brewers to adjust pH. Fermentation continued until the fermentate contained about 15.6% ethanol.

The fermentate was then separated into three, five-liter samples, one of which was designated as the negative control, and the other two designated as test samples. The control sample was not treated with Enzyme 2, the first test sample was treated with Enzyme 2 at a loading of 1:1000 at 90° F. and a pH of 6.7, and the second test sample was treated with Enzyme 2 (loading of 1:1000) and a dinucleotide cofactor (NAD+) at 91° F. and a pH of 6.7. The control sample had 15.6% ABV, the first test sample had an approximately 12% ABV, and the second test sample had an approximately 13% ABV.

Each sample was distilled at initial pressures of about 2.5 psi and boiling temperatures of about 130° F. The same percentage of volume for the hearts at 125 to 135 proof was collected for each sample, and the final distillates diluted to 80 proof.

Sensory testing was done subsequently to determine if the impact on harshness was easily detectable. The control sample and each test sample were tasted by 30 test subjects. Relative to the control sample, the first test sample and the second test sample exhibited harshness level reductions of 85% and 100%, respectively. Accordingly, adding the aldehyde dehydrogenase to the fermentate drastically reduced the final harshness level of the un-aged whiskey, with the combination of aldehyde dehydrogenase and a cofactor having an especially significant effect. This data shows that from the hundreds of compounds created during fermentation, those responsible for harshness were eliminated or reduced to levels below sensory detection by admixing an aldehyde dehydrogenase with a fermentate, and by admixing a combination of the aldehyde dehydrogenase and a cofactor with a fermentate, and forming distilled alcoholic beverages from the enzymatically treated fermentates.

The ability of the enzymes to act on multiple aldehydes present at very low levels at a unique range of pH and temperature typically seen in these types of fermentations was further evaluated via tasting by additional subjects, who tasted the samples independently and reported their results separately. Effective oxidation of the targeted aldehydes by the aldehyde dehydrogenase was determined by collecting sensory data generated from the test subjects after consuming distilled alcoholic beverages either treated or not treated with the enzyme.

All 30 subjects not only distinguished between the treated and untreated samples, but were able to clearly identify which sample was treated and which sample was not treated based on the greater relative harshness of the untreated samples.

Experiment 5—2nd Distiller Trial with Enzyme 3: Testing a Vodka

In this experiment, the ability of Enzyme 3 (corresponding to SEQ ID NO: 8) to drastically reduce the harshness compounds and therefore sensory perception using co-factor NADP on a vodka was demonstrated. A vodka mash was created using a white winter wheat malt by adding water and calcium chloride and heating to 152° F. for an hour. After cooling to 70° F. and aerating, yeast starter and yeast nutrients were added to start fermentation. At the end of fermentation, pH was controlled using baking soda, maintaining it at pH of 6.5. A portion of this fermented liquid was treated with Enzyme 3 (loading of 1:1000) and a cofactor (NADP+) at 86° F. for 24 hours prior distillation. At the end of fermentation, the fermentate ABV was 9.4% heading into distillation. The fermentates were distilled and heads collected at 184 proof and subsequently diluted to 80 proof for tasting.

Sensory testing was then done by ten people, tasting the control samples versus the enzyme-treated samples. All ten of the test subjects were able to clearly identify the treated samples as at least 80% smoother, marked by the elimination of the harsh bite experienced upon consumption of the control samples.

Experiment 6—Testing with Native and Genetically Engineered Enzymes

Figure 16:
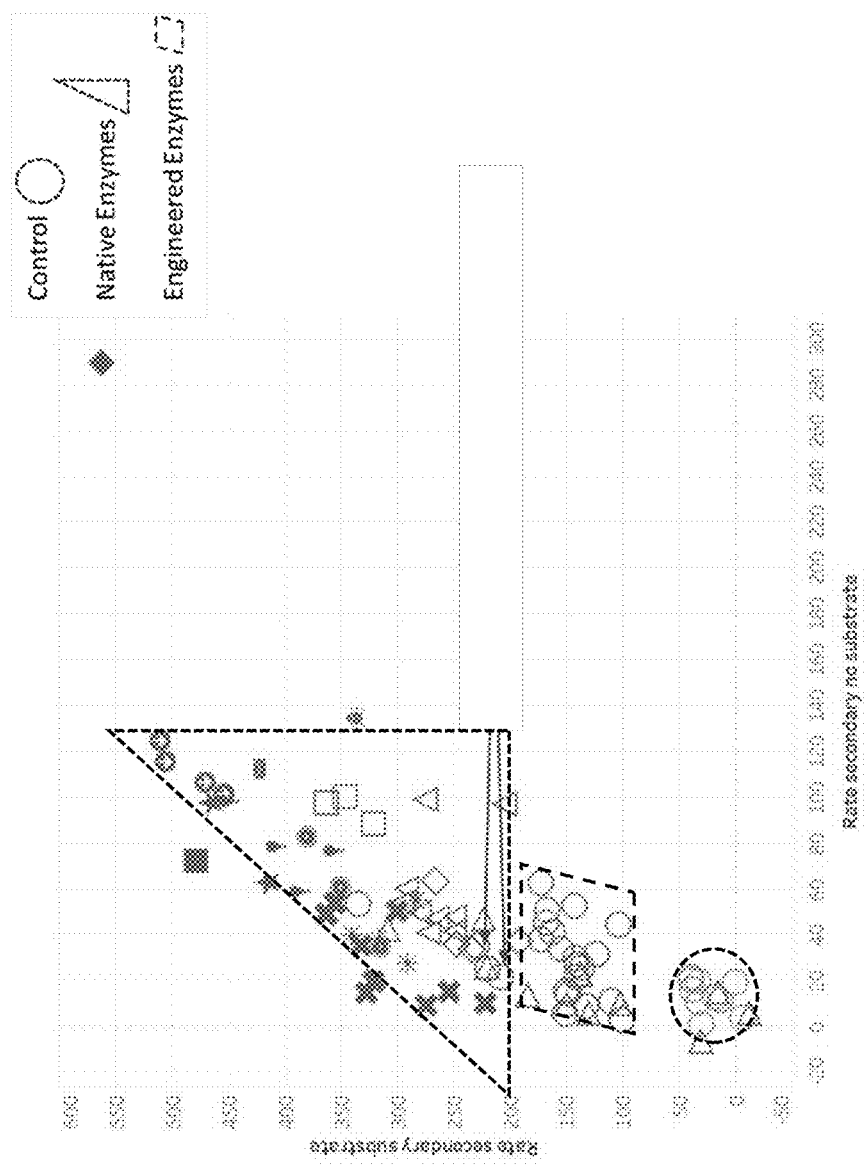
FIG. 16 is a graph showing the substrate catalysis activity of various engineered and native forms of aldehyde dehydrogenase.

To demonstrate that native oxidase enzymes as well as engineered oxidase enzymes are effective alcohol harshness reducers, a series of tests were conducted to illustrate the efficacy of engineered enzymes to also catalyze very specific reactions that convert the compounds responsible for the harshness. As shown in FIG. 16, the activity of native dehydrogenases corresponding to SEQ ID NOS: 1-17 and dehydrogenases engineered from enzymes having SEQ ID NOS: 1-17 exhibited effective substrate catalysis, evidenced by the robust rate of target substrate catalysis exhibited for the native enzymes (grouped in the dashed triangle) and engineered enzymes (grouped in the dashed parallelogram). By comparison, samples not treated with any forms of the enzymes exhibited little to no substrate catalysis (grouped in the dashed circle). These data further indicate that a variety of aldehyde dehydrogenases, native or engineered, may be utilized pursuant to the methods disclosed herein to catalyze substrates identified as causing the harsh bite typically associated with consumable alcoholic beverages and components thereof.

The above description of certain embodiments is merely exemplary in nature and is in no way intended to limit the disclosed implementations or their applications or uses. Reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. It is to be appreciated, for instance, that any one of the examples, embodiments or processes described herein may be combined with one or more other examples, embodiments and/or processes or be separated and/or performed amongst separate devices or device portions in accordance with the present systems, devices and methods. Moreover, for the purpose of clarity, detailed descriptions of certain features were not discussed when they would be apparent to those with skill in the art so as not to obscure the description of the present system. This detailed description is therefore not to be taken in a limiting sense, and the scope of the present system is defined only by the appended claims.

What is claimed is:

1. A method of producing a consumable alcoholic product, the method comprising:
    forming a mash mix;
    fermenting the mash mix to form a fermentate;
    oxidizing at least one aliphatic aldehyde present within the fermentate by admixing at least one oxidase with the fermentate; and
    collecting the fermentate for inclusion in the consumable alcoholic product.

2. The method of claim 1, wherein the at least one oxidase comprises an aldehyde dehydrogenase.

3. The method of claim 2, wherein the aldehyde dehydrogenase is a native aldehyde dehydrogenase.

4. The method of claim 2, wherein the aldehyde dehydrogenase is an engineered or modified aldehyde dehydrogenase.

5. The method of claim 1, wherein the aliphatic aldehydes comprise C2-C10 aliphatic aldehydes.

6. The method of claim 5, wherein the consumable alcoholic product has a lower level of aliphatic aldehydes relative to a level of aliphatic aldehydes present in a consumable alcoholic product not admixed with the at least one dehydrogenase.

7. The method of claim 6, wherein the level of aliphatic aldehydes present in a consumable alcoholic product not admixed with the at least one oxidase ranges from a concentration in a range spanning ppm to ppb.

8. The method of claim 1, further comprising admixing at least one dinucleotide cofactor with the fermentate.

9. The method of claim 8, wherein the dinucleotide cofactor comprises NAD+, NADP+, or both.

10. The method of claim 1, further comprising distilling the fermentate to form a distilled ethanol comprising or formulated for inclusion in the consumable alcoholic product.

11. The method of claim 10, further comprising aging the distilled ethanol in a barrel.

12. The method of claim 11, wherein an ethanol concentration of the distilled ethanol is about 20% to about 95%.

13. The method of claim 1, wherein the consumable alcoholic product comprises a beer.

14. The method of claim 1, further comprising adjusting a pH of the fermentate to about 5.0 to about 7.0.

15. The method of claim 1, wherein a pH of the fermentate is not adjusted.

16. The method of claim 1, wherein the at least one oxidase is added at a loading level of about 5 mg/L to about 2 g/L of a fermentation volume.

17. The method of claim 1, wherein fermenting the mash mix comprises fermenting the mash mix for about up to about 5days.

18. The method of claim 1, wherein the mash mix comprises one or more of corn, rye, rice, barley, wheat, agave, dextrin, potato, fruit, molasses, water, an enzyme, a sugar source, or sucrose.

19. The method of claim 1, wherein an ethanol concentration of the fermentate is about 1% to about 20%.

20. A method of producing a consumable alcoholic product, the method comprising:
    fermenting a mash mix to form a fermentate;
    oxidizing at least one aliphatic aldehyde produced via lipid peroxidation and present within the fermentate by admixing at least one oxidase with the fermentate; and
    collecting the fermentate for inclusion in the consumable alcoholic product.

* * * * *

SEQUENCE LISTING

```
Sequence total quantity: 17
SEQ ID NO: 1           moltype = AA  length = 495
FEATURE                Location/Qualifiers
source                 1..495
                       mol_type = protein
                       organism = synthetic construct
SEQUENCE: 1
MHHHHHHGGS GMELEVRRVR QAFLSGRSRP LRFRLQQLEA LRRMVQEREK DILTAIAADL   60
CKSEFNVYSQ EVITVLGEID FMLENLPEWV TAKPVKKNVL TMLDEAYIQP QPLGVVLIIG  120
AWNYPFVLTI QPLIGAIAAG NAVIIKPSEL SENTAKILAK LLPQYLDQDL YIVINGGVEE  180
TTELLKQRFD HIFYTGNTAV GKIVMEAAAK HLTPVTLELG KSPCYIDKDC DLDIVCRRIT  240
WGKYMNCGQT CIAPDYILCE ASLQNQIVWK IKETVKEFYG ENIKESPDYE RIINLRHFKR  300
ILSLLEGQKI AFGGETDEAT RYIAPTVLTD VDPKTKVMQE EIFGPILPIV PVKNVDEAIN  360
FINEREKPLA LYVFSHNHKL IKRMIDETSS GGVTGNDVIM HFTLNSFPFG GVGSSGMGAY  420
HGKHSFDTFS HQRPCLLKSL KREGANKLRY PPNSQSKVDW GKFFLLKRFN KEKLGLLLLT  480
FLGIVAAVLV KAEYY                                                   495

SEQ ID NO: 2           moltype = AA  length = 519
FEATURE                Location/Qualifiers
```

```
source                          1..519
                                mol_type = protein
                                organism = synthetic construct
SEQUENCE: 2
MHHHHHHGGS GMEREVQRVR QAFLSGRSRP LRFRLQQLEA LRRMVQEREK DILAAIAADL    60
CKSELNAYSQ EVITVLGEID FMLENLPEWV TAKPVKKNLL TMMDEAYIQP QPLGVVLIIG   120
AWNYPFVLII QPLIGAIAAG NAVIIKPSEL SENTAKIVAK LLPQYLDQDL YVVINGGVEE   180
TTELLKQRFD HIFYTGNTAV GKIVMEAAAK HLTPVTLELG GKSPCYIDKD CDLDIVCRRI   240
TWGKYMNCGQ TCIAPDYILC EASLQSQIVW KIKETVKEFY GENIKESPDY ERIINLRHFK   300
RILSLLEGQK IALGGETDEA TRYIAPTVLT DVDPKTKVMQ EEIFGPVLPI VPVKNVDEAI   360
DFINEREKPL ALYVFSHNHK LIKRMIDETS SGGVTGNDVI MHFTLNSPPF GGVGSSGMGA   420
YHGKHSFDTF SHQRPCLLKS LKREGANKLR YPPNSQSKVD WGKFFLLRRF NKEKLGLLVL   480
TFLGIVAAVL VKKYQAVLRR KALLIFLVVH RLRWSSKQR                          519

SEQ ID NO: 3                    moltype = AA  length = 496
FEATURE                         Location/Qualifiers
source                          1..496
                                mol_type = protein
                                organism = synthetic construct
SEQUENCE: 3
MHHHHHHGGS GMEREVQRVR QAFRSGRSRP LRFRLQQLEA LRRMVLEREK DILAAIGADL    60
CKSEFNAYSQ EVITVLGEID FMLENLPEWI TAKSVKKNLL TMLDEAYVQP EPLGVVLIIG   120
AWNYPFVLTI HPLVGAIAAG NAVIIKPSEL SENTATILAK LLPQYLDQDL YAVVNGGVKE   180
TTELLKQRFD HILYTGSAAV GKIVMEAAAK HLTPVTLELG GKSPCYIDKD CDLDIVCRRI   240
TWGKYMNCGQ TCIAPDYILC EASLQDQIVQ KIKETVKEFY GENIKESPDY ERIINPRHFK   300
RILSLLEGQK IAFGGETDED TRYIAPTILT DVDPETKVMQ EEIFGPILPI VPVKNVDEAI   360
NFINEREKPL ALYVFSHNSK LIKRMIDETS SGGVTGNDVI MHFILNSLPF GGVGSSGMGA   420
YHGKYSFDTF SHQRPCLLKS LKGEAANKLR YPPNSQSKVD WGKFFFLKRF NKGKLSLLLL   480
AFLGVLAAVL IKAGYY                                                   496

SEQ ID NO: 4                    moltype = AA  length = 648
FEATURE                         Location/Qualifiers
source                          1..648
                                mol_type = protein
                                organism = synthetic construct
SEQUENCE: 4
MHHHHHHGGS GMIATKWRRD EEPLSRASVC VGRVLSRWRG TYCLAPASLQ RFGHSISAPQ    60
LTSPGLFVPG PGATHPPAAF LTSHPRFQGV GGAGVRLSRS RVPLRPIGAP PRVEPSPAGW   120
VDLGQLDAAG TEDFVGSSGE QGKAMEREVQ RARIAFGSGR SRPLRFRLQQ LEALRRMVQE   180
REKDILAAIA SDLCKSEFNV YSQEVITILG EIDLVLENLP EWVTAKPAKK NLFTMLDEAY   240
VQPEPFGVVL IIGAWNYPFV LTIHPLIGAI AAGNAVIIKP SELCENTAKI LSKLLPQYLD   300
QDLYIVINGG VEETTELLKQ RFDHILFTGS PSVGKIVMEA AAKHLTPVTL ELGGKNPCYI   360
DKDCDLDVAC RRIAWGKYMN CGQICIAPDY ILCEPSLQNQ IVQKIKENVK EFYGENVKES   420
PDYERIINLR HFKRIISLLE GQKIAFGGET DEATRYIAPT ILTDVNPETK VMQEEIFGPI   480
LPIVPVKNAD EAIKFINERE KALTFYVFSH NKKLVKQMID GTSSGAVTVN DVIMHFTLSS   540
LPFGGVGSSG MGTYHGKYSF DTFSHQRSCL LKSLKMEGVN KLRYPPNSQS KVDWAKFFLL   600
KRISKRTLSL LFLAFLGIVA AVLVKDISPQ PDMHLLGWNL EVRADCTL                648

SEQ ID NO: 5                    moltype = AA  length = 523
FEATURE                         Location/Qualifiers
source                          1..523
                                mol_type = protein
                                organism = synthetic construct
SEQUENCE: 5
MHHHHHHGGS GMTNNPPSAQ IKPGEYGFPL KLKARYDNFI GGEWVAPADG EYYQNLTPVT    60
GQLLCEVASS GKRDIDLALD AAHKVKDKWA HTSVQDRAAI LFKIADRMEQ NLELLATAET   120
WDNGKPIRET SAADVPLAID HFRYFASCIR AQEGGISEVD SETVAYHFHE PLGVVGQIIP   180
WNFPLLMASW KMAPALAAGN CVVLKPARLT PLSVLLLMEI VGDLLPPGVV NVVNGAGGVI   240
GEYLATSKRI AKVAFTGSTE VGQQIMQYAT QNIIPVTLNA GSSPNIFFA DVMDEEDAFF   300
DKALEGFALF AFNQGEVCTC PSRALVQESI YERFMERAIR RVESIRSGNP LDSVTQMGAQ   360
VSHGQLETIL NYIDIGKKEG ADVLTGGRRK LLEGELKDGY YLEPTILFGQ NNMRVFQEEI   420
FGPVLAVTTF KTMEEALELA NDTQYGLGAG VWSRNGNLAY KMGRGIQAGR VWTNCYHAYP   480
AHAAFGGYKQ SGIGRETHKM MLEHYQQTKC LLVSYSDKPL GLF                     523

SEQ ID NO: 6                    moltype = AA  length = 499
FEATURE                         Location/Qualifiers
source                          1..499
                                mol_type = protein
                                organism = synthetic construct
SEQUENCE: 6
MHHHHHHGGS GMKVQTEIKT YFNYINGNWV SSVSNNVEPS INPANRHDIV GYVQRSTLED    60
VNEAVTAANE AQTSWWKRSG VERGEYLYKA AHILEQCLQD IAETMTREMG KTLAEAKAET   120
MRGVHILRYY AGEGARKIGD VIPSSDSEGL LFTTRVPLGV VGVISPWNFP VAIPIWKMAP   180
ALVYGNTVVL KPASETAVTA AKVIECFHEA GFPKGVVNMV CGSGSVVGQG IANHPDIDGV   240
TPFTGSNTVGK QVGRAAFERG AKYQLEMGGK NPVIVAKDAD LDLAVEGTIS GGLRSTGQKC   300
TATSRVFIER EVYEPPKAKL LERVKQLKIG NGLDAETWMG PCASESQFHT VLSYIEKGKS   360
EGAKLIYGGN RCLEGELANG FFVEPTIFED VDLQMTIARE EIFGPVLALI QVDSIEEAIK   420
LANDTEYGLS ASIYTKNIGN ALEFIKDIEA GLIKVNAETA GVEFQAPFGG MKQSSSHSRE   480
QGQAAIEFFT SIKTVFVKA                                                499
```

```
SEQ ID NO: 7              moltype = AA  length = 499
FEATURE                   Location/Qualifiers
source                    1..499
                          mol_type = protein
                          organism = synthetic construct
SEQUENCE: 7
MHHHHHHGGS GMTVQTEIKT YLNYINGKWV SSASNNVEPS INPANRHDIV GYVQRSTLED    60
VNEAVAAAKQ AQPSWWKRSG VERGEYLYKA AQILEQRLQD IAETMTREMG KTLAEAKAET   120
MRGVHILRYY AGEGARKIGD VIPSSDSEGL LFTTRVPLGV VGVISPWNFP VAIPIWKMAP   180
ALVYGNTVVL KPASETAVTA AKVIECFHEA GFPEGVVNMV CGSGSVIGQG IANHPDVDGV   240
TFTGSNTVGK QVGRAAFERG AKYQLEMGGK NPVIVAKDAD LELAVEGTIS GGLRSTGQKC   300
TATSRVFIER EVYEAFKEKL LERVKQLKIG NGLDAETWMG PCASKSQFNT VLSYIEKGKA   360
EGAKLIYGGN RCLEGELANG FYVEPTIFED VDIQMTIARE EIFGPVLALI QVDSIEEAIQ   420
LANDTEYGLS ASIYTKNIGN VLEFIKDIEA GLIKVNAETA GVEFQAPFGG MKQSSSHSRE   480
QGQAAIEFFT SIKTVFVKA                                                499

SEQ ID NO: 8              moltype = AA  length = 499
FEATURE                   Location/Qualifiers
source                    1..499
                          mol_type = protein
                          organism = synthetic construct
SEQUENCE: 8
MHHHHHHGGS GMAVQTEIKT YLNYIDGSWV GSVSKNVEPS INPANRNDIV GYVPRSTLED    60
LNAAVAAAKQ AQKSWWKRSG IERGEYLYKA ALLLEQRLED IAETMTREMG KTLAEAKAET   120
MRGVHILRYY AGEGARKIGD VIPSSDSGGL MFTTRVPLGV VGVISPWNFP VAIPIWKMAP   180
ALVYGNTVVL KPASETAVTA AKVIECFHEA GFPKGVVNMV CGSGSVIGQG IANHPDVDGV   240
TFTGSNTVGK QVGRAAFERG AKYQLEMGGK NPVIVAKDAD LDLAVEGTIS GGLRSTGQKC   300
TATSRVFIER EVYEPFKEKL LERVKQLKIG NGMDAETWMG PCASESQLNT VLSYIEKGKA   360
EGAKLIYGGN RCTEGELANG FYVEPTIFEE VDLQMTIARE EIFGPVLVLI PVDSIEEAIE   420
LANDTEYGLS ASIYTKNIGN ILDFIKDIEA GLVKVNAETA GVEYQAPFGG MKQSSSHSRE   480
QGQAAIEFFT TIKTVFVKA                                                499

SEQ ID NO: 9              moltype = AA  length = 499
FEATURE                   Location/Qualifiers
source                    1..499
                          mol_type = protein
                          organism = synthetic construct
SEQUENCE: 9
MHHHHHHGGS GMTVQTEVKT YFNYINGEWV SSVTNEVEAS INPANKNEVV GYIQRSSIED    60
LNEAVAAAKR AQKSWRKRSG VERGEYLYRA ADILERRLEE IAETMTREMG KTFGEAKAET   120
MRGVHILRYY AGEGVRKIGD VIPSSDNEAL MFTTRVPLGV VGVISPWNFP VAIPIWKMAP   180
ALVYGNTVVL KPASEAAITA AKVIECFHEA GFPKGVVNMI CGPGSVIGQG IANHPDIGV    240
TFTGSNTVGK LVGKAAFERG AKYQLEMGGK NPVIVAKDAD LDLAVEGTIN GGLRSTGQKC   300
TATSRVFVES EVYETFKEKL LAKVKQLKIG NGMDSETWMG PCVSEAQLNT VLSYIEKGKA   360
EGADLIYGGK RCIEGEFANG FYVEPTIFEN VDINMTIARE EIFGPVLALI KVHSIEEALE   420
LANDTEYGLS ASIYTKDISN ILSFINEIEA GLVKVNAETA GVEFQAPFGG MKQSSSHSRE   480
QGQAAIEFFT SIKTVLVKA                                                499

SEQ ID NO: 10             moltype = AA  length = 506
FEATURE                   Location/Qualifiers
source                    1..506
                          mol_type = protein
                          organism = synthetic construct
SEQUENCE: 10
MHHHHHHGGS GMNFHHLAYW QDKALSLAIE NRLFINGEYT AAAENETFET VDPVTQAPLA    60
KIARGKSVDI DRAMSAARGV FERGDWSLSS PAKRKAVLNK LADLMEAHAE ELALLETLDT   120
GKPIRHSLRD DIPGAARAIR WYAEAIDKVY GEVATTSSHE LAMIVREPVG VIAAIVPWNF   180
PLLLTCWKLG PALAAGNSVI LKPSEKSPLS AIRLAGLAKE AGLPDGVLNV VTGFGHEAGQ   240
ALSRHNDIDA IAFTGSTRTG KQLLKDAGDS NMKRVWLEAG GKSANIVFAD CPDLQQAASA   300
TAAGIFYNQG QVCIAGTRLL LEESIADEFL ALLKQQAQNW QPGHPLDPAT TMGTLIDCAH   360
ADSVHSFIRE GESKGQLLLD GRNAGLAAAI GPTIFVDVDP NASLSREEIF GPVLVVTRFT   420
SEEQALQLAN DSQYGLGAAV WTRDLSRAHR MSRRLKAGSV FVNNYNDGDM TVPFGGYKQS   480
GNGRDKSLHA LEKFTELKTI WISLEA                                        506

SEQ ID NO: 11             moltype = AA  length = 506
FEATURE                   Location/Qualifiers
source                    1..506
                          mol_type = protein
                          organism = synthetic construct
SEQUENCE: 11
MHHHHHHGGS GMNFHHLAYW QDKALNLALE TRLFINGEYC AAADGTTFET IDPFSEVPLA    60
NIARGKSADI DFAVKGARAV FESGVWSNAA PAKRKAALNK LADLIEANAE ELALLETLDT   120
GKPIRHSLRD DVPGAARAIR WYAEALDKVY GEVATTGSQE LAMIVREPVG VVAAIVPWNF   180
PLLLTCWKLG PALAAGNSVI LKPSEKSPLT ALRLAGLAKE AGIPDGVLNV VSGFGHEAGQ   240
ALSRHPDIDV IAFTGSTRTG KQLLKDAGDS NMKRVWLEAG GKSANIVFAD CPDLQQAVSA   300
TASGIFYNQG QVCIAGTRLL LEDSIADEFL NLLQQQISHW QPGHPLDPST TMGTLIDSAH   360
ADTVHSFIRD GEQKGQLLVD GRQTAWPAAI GPTIFVDVDP EDRLSQEEIF GPVLVVTRFT   420
SEEQALALAN NSQYGLGAAV WTRDLSRAHR LSRRLKAGSV FVNNYNDGDM TVPFGGYKQS   480
```

```
GNGRDKSLHA LDKFTEIKTI WISLEA                                    506

SEQ ID NO: 12           moltype = AA  length = 506
FEATURE                 Location/Qualifiers
source                  1..506
                        mol_type = protein
                        organism = synthetic construct
SEQUENCE: 12
MHHHHHGGS GMNFHHLAYW QDKALSLAIE NRLFINGEYT AAAENETFET VDPVTQAPLA   60
KIARGKSVDI DHAVSAARGV FERGDWSLSS PAKRKAVLNK LADLMEAHAE ELALLETLDT  120
GKPIRHSLRD DIPGAARAIR WYAEAIDKVY GEVATTSSHE LAMIVREPVG VIAAIVPWNF  180
PLLLTCWKLG PALAAGNSVV LKPSEKSPLS AIRLAGLEKE AGLPDGVLNV VTGFGHEAGQ  240
ALSRHDDIDA IAFTGSTRTG KQLLKDAGDS NMKRVWLEAG GKSANIVFAD CPDLQKAVSA  300
TAAGIFYNQG QVCIAGTRLL LEESIADEFL ALLKQQAQNW QPGHPLDPAT TMGTLIDCAH  360
ADSVHSFIRE GESKGQLLLD GRNAELAAAI GPTIFVDVDP NASLSREEIF GPVLVVTRFT  420
SEDQALQLAN DSQYGLGAAV WTRDLSRAHR MSRRLKAGSV FVNNYNDGDM TVPFGGYKQS  480
GNGRDKSLHA LEKFTELKTI WISLEA                                    506

SEQ ID NO: 13           moltype = AA  length = 506
FEATURE                 Location/Qualifiers
source                  1..506
                        mol_type = protein
                        organism = synthetic construct
SEQUENCE: 13
MHHHHHGGS GMNFQHLAYW QEKAKNLAIE TRLFINGEYC AAADNTTFET IDPAAQQTLA   60
QVARGKKADV ERAVKAARQA FDNGDWSQAS PAQRKAILTR FADLMEAHRE ELALLETLDT  120
GKPIRHSLRD DIPGAARAIR WYAEALDKVY GEVAPTGSNE LAMIVREPIG VIAAVVPWNF  180
PLLLACWKLG PALAAGNSVI LKPSEKSPLT ALRLAGLAKE AGLPDGVLNV VSGFGHEAGQ  240
ALALHPDVEV ITFTGSTRTG KQLLKDAGDS NMKRVWLEAG GKSANIVFAD CPDLQQAVRA  300
TAGGIFYNQG QVCIAGTRLL LEESIADEFL ARLKAEAGHW QPGNPLDPDT TMGMLIDNTH  360
ADNVHSFIRG GESQSTLFLD GRKNPWPAAV GPTIFVDVDP ASTLSREEIF GPVLVVTRFK  420
SEEEALKLAN DSDYGLGAAV WTRDLSRAHR MSRRLKAGSV FVNNYNDGDM TVPFGGYKQS  480
GNGRDKSLHA LEKFTELKTI WIALES                                    506

SEQ ID NO: 14           moltype = AA  length = 514
FEATURE                 Location/Qualifiers
source                  1..514
                        mol_type = protein
                        organism = synthetic construct
SEQUENCE: 14
MHHHHHGGS GMHYVDPNQS GSKIHFKDQY ENFIGGQWVA PVKGVYFDNI SPVDGKSFTR   60
IPRSSAEDIE LALDAAHKAK KEWNKSSPTT RSNLLLKIAD RMEANLEMLA VAETWDNGKP  120
VRETLAADIP LAIDHFRYFA GCIRAQEGGI SEIDEDTIAY HFHEPLGVVG QIIPWNFPIL  180
MAAWKLAPAL AAGNCVVIKP AEQTPVGILL VAELIQDLLP AGVLNIVNGY GAEVGRPLAT  240
SPRIAKIAFT GSTQVGQLIM QYATENIIPV TLELGGKSPN VFFADVMDHD DDFLDKTLEG  300
FAMFALNQGE VCTCPSRALI QESIADQFME KAIERVKRIK LGHPLDTDTM VGAQASLEQQ  360
EKILRCIDTG RQEGAEVLLG GHGRQEVGNG YYIEPTIFKG HNNMQVFQEE IFGPVLSVTT  420
FKDFDEAIQI ANDTMYGLGA GVWSRSTHTA YRAGRAIEAG RVWTNCYHIY PAHAAFGGYK  480
KSGVGRENHK MMLDHYQQTK NLLVSYSTKA MGFF                           514

SEQ ID NO: 15           moltype = AA  length = 514
FEATURE                 Location/Qualifiers
source                  1..514
                        mol_type = protein
                        organism = synthetic construct
SEQUENCE: 15
MHHHHHGGS GMRYIDPNQP DSKIHFKAQY ENFIGGQWVA PVKGVYFDNI SPVDGKSFTR   60
IPRSSAEDIE LALDAAHKAK KEWNKSSPTT RSNLLLKIAD RMEANLEMLA VAETWDNGKP  120
VRETLAADIP LAIDHFRYFA GCIRAQEGGI SEIDEDTIAY HFHEPLGVVG QIIPWNFPIL  180
MAAWKLAPAL AAGNCVVIKP AEQTPVGILL VAELIQDLLP AGVLNIVNGY GAEVGQPLAT  240
NPRIAKIAFT GSTQVGQLIM RYATENIIPV TLELGGKSPN LFFADVMDQD DDFLDKTLEG  300
FAMFALNQGE VCTCPSRALI QESIADQFME KAIERVKRIK LGHPLDTETM VGAQASLEQQ  360
QKILRCIDTG RQEGAEVLLG GHDRKEVGNG YYIEPTIFKG HNNMQVFQEE IFGPVLSVTT  420
FKDFDEAIQI ANDTMYGLGA GVWSRSTHTA YRAGRAIEAG RVWTNCYHIY PAHAAFGGYK  480
KSGVGRENHR MMLDHYQQTK NLLVSYSTKA MGFF                           514

SEQ ID NO: 16           moltype = AA  length = 514
FEATURE                 Location/Qualifiers
source                  1..514
                        mol_type = protein
                        organism = synthetic construct
SEQUENCE: 16
MHHHHHGGS GMRYIDPNQP NSKVQFKPQY ENFIGGQWVA PTRGEYFDNV SPVDGKVFTK   60
IPRSSVEDIE LALDAAHKAK AEWNKSSPTF RSNILLKIAD RMEANLEMLA VAETWDNGKP  120
VRETLAADIP LAIDHFRYFA GCIRAQEGGI SEIDEDTIAY HFHEPLGVVG QIIPWNFPIL  180
MAAWKLAPAL AAGNCVVLKP AEQTPVGILL VLELIQDLLP AGVLNVINGY GAEVGRPLAT  240
SPRIAKIAFT GSTQVGQLIM QYATENIIPV TLELGGKSPN IFFEDIMDKE DDFLDKALEG  300
FAMFALNQGE VCTCPSRALV QESIADAFLE KAIERVKRIK VGHPLDTETM IGAQASLEQQ  360
EKILRCISTG REEGAELLTG GSARQEVGEG FYIEPTVFKG HNSMQIFQEE IFGPVLSVTT  420
```

```
FKDFDEAIQI ANETIYGLGA GVWARSAHTS YRAGRAVEAG RVWTNCYHIY PAHAAFGGYK    480
KSGIGRENHR MMLDHYQQTK NLLVSYSTKP AGFF                                514

SEQ ID NO: 17           moltype = AA  length = 514
FEATURE                 Location/Qualifiers
source                  1..514
                        mol_type = protein
                        organism = synthetic construct
SEQUENCE: 17
MHHHHHHGGS GMRYIDPNQS GSKVQFKSQY ENFIGGEWVA PVKGAYFDNV SPVDGKAFTR    60
IPRSSAEDIE LALDAAHKAK ATWNKASPTV RSNILLKIAD RLEANLEMLA VAETWDNGKA    120
VRETLAADIP LAIDHFRYFA GCIRAQEGGI SEIDEDTIAY HFHEPLGVVG QIIPWNFPIL    180
MAAWKLAPAL AAGNCVVIKP AEQTPVGILL VAELIQDILP PGVLNIVNGF GAEVGRPLAT    240
NPRIAKIAFT GSTQTGQMVM QYATENIIPV TLELGGKSPN LFFEDIMDKE DDFLEKTLEG    300
FAMFALNQGE VCTCPSRALV QESIADQFLE MAVERVKRIK TGHPLDTETM IGAQASLQQQ    360
EKILSCINTG REEGAELLLG GSGRKEVGDG FYVDPTIFKG HNSMQIFQEE IFGPVLAVTT    420
FKDFDDAIKI ANDTMYGLGA GVWSRSAHIS YRAGRAIEAG RVWTNCYNIY PAHAAFGGYK    480
KSGIGRENHK MMLDHYQQTK NLLVSYSTKP MGFF                                514
```